US008283123B2

(12) United States Patent
Vuolteenaho et al.

(10) Patent No.: US 8,283,123 B2
(45) Date of Patent: Oct. 9, 2012

(54) METHODS OF DETERMINATION OF ACTIVATION OR INACTIVATION OF ATRIAL NATRIURETIC PEPTIDE (ANP) AND BRAIN NATRIURETIC PEPTIDE (BNP) HORMONAL SYSTEMS

(75) Inventors: Olli Vuolteenaho, Oulu (FI); Minna Ala-Kopsala, Oulu (FI); Heikki Ruskoaho, Tyrnava (FI); Juhani Leppäluoto, Oulu (FI); Jouko Haapalahti, Kempele (FI)

(73) Assignee: Orion Diagnostica Oy, Espoo (FI)

( * ) Notice: Subject to any disclaimer, the term of this patent is extended or adjusted under 35 U.S.C. 154(b) by 236 days.

(21) Appl. No.: 10/562,081

(22) PCT Filed: Jun. 28, 2004

(86) PCT No.: PCT/EP2004/006971
§ 371 (c)(1),
(2), (4) Date: Apr. 5, 2006

(87) PCT Pub. No.: WO2005/003764
PCT Pub. Date: Jan. 13, 2005

(65) Prior Publication Data
US 2007/0141634 A1 Jun. 21, 2007

(30) Foreign Application Priority Data

Jun. 30, 2003 (GB) .................................. 0315291.5

(51) Int. Cl.
*G01N 33/53* (2006.01)
*G01N 33/00* (2006.01)
(52) U.S. Cl. ....... 435/7.1; 435/7.92; 435/7.93; 435/7.94
(58) Field of Classification Search .................. None
See application file for complete search history.

(56) References Cited

U.S. PATENT DOCUMENTS

| 5,212,286 | A | * | 5/1993 | Lewicki et al. ............... 530/324 |
| 5,747,274 | A | | 5/1998 | Jackowski |
| 5,786,163 | A | | 7/1998 | Hall |
| 6,117,644 | A | | 9/2000 | DeBold |
| 6,124,430 | A | | 9/2000 | Mischak et al. |
| 6,461,828 | B1 | | 10/2002 | Stanton et al. |
| 6,818,619 | B2 | * | 11/2004 | Burnett et al. ............... 514/12 |
| 7,341,838 | B2 | * | 3/2008 | Buechler et al. ............ 435/7.1 |

FOREIGN PATENT DOCUMENTS

| AU | 200025451 B2 | 8/2000 |
| EP | 0 393 640 | 10/1990 |
| EP | 0 542 255 | 5/1993 |
| EP | 0 648 228 | 11/1998 |
| EP | 1 118 329 | 7/2001 |
| WO | WO 87/06938 | 11/1987 |
| WO | WO 91/00292 | 1/1991 |
| WO | WO 93/24531 | 12/1993 |
| WO | WO 95/28952 | 11/1995 |
| WO | WO 00/19207 | 4/2000 |
| WO | WO 00/35951 | 6/2000 |
| WO | WO 00/45176 | 8/2000 |
| WO | WO 00/71576 | * 11/2000 |
| WO | WO 01/79231 A2 | * 10/2001 |
| WO | WO 02/074234 | 9/2002 |

OTHER PUBLICATIONS

Clerico et al. 2000. Clin. Chemistry 46:1529-1534.*
Tremblay et al 2002. Mol and Cell Biochem. 230:31-47.*
Flashner et al.1996. Mol Microbiol. 19:985.*
Parkhill et al. 2001. Nature 413:848.*
Solomon et al. 1992. Yeast 8:273.*
Stover et al 2000. Nature 406:959.*
Wang et al 2001. J. Biol Chem. 276:49213-49220.*
Swartzman et al. 1999. Analytical Biochem. 271:143-151.*
Parkhill et al 2000. Nature 403:665.*
Veale et al. 2000. Bioorganic and Medicinal Chem Let. 10:1949-1952.*
Paul, Fundamental Immunology, 3r~ Edition, 1993, pp. 292-295, under the heading "Fv Structure and Diversity in Three Dimensions".*
Rudikoff et al Proc. Natl. Acad. Sci.USA, 79(6):1979-1983, Mar. 1982.*
Colman P. M. Research in Immunology, 145:33-36, 1994.*
"Atrial Natriuretic Peptide Receptor A Precursor," Swiss-ProtID ANPA_HUMAN Standard; PRT; 1061 AA; AC P16066; Apr. 1, 1990, downloaded Jun. 17, 2003.
"Atrial Natriuretic Peptide Receptor B Precursor," Swiss-Prot ID ANPB_HUMAN Standard; PRT; 1047 AA; AC P20594, O60871, Q9UQ50; Feb 1, 1991, downloaded Jun. 17, 2003.
Buckley et al., "Plasma Concentrations and Comparisons of Brain Natriuretic Peptide and Atrial Natriuretic Peptide in Normal Subjects, Cardiac Transplant Recipients and Patients with Dialysis-Independent or Dialysis-Dependent Chronic Renal Failure," Clin. Sci. 83:437-444, 1992.
Clerico et al., "Circulating Levels of Cardiac Natriuretic Peptides (ANP and BNP) Measured by Highly Sensitive and Specific Immunoradiometric Assays in Normal Subjects and in Patients with Different Degrees of Heart Failure," J. Endocrinol. Invest 21:170-179, 1998.
Daly et al., "Natriuretic Peptides in the Diagnosis of Heart Disease—First Amongst Equals?" Int. J. Cardiol. 84:107-113, 2002.
De Lemos et al., "The Prognostic Value of B-Type Natriuretic Peptide in Patients with Acute Coronary Syndromes," N. Engl. J. Med. 345:1014-1021, 2001.
Donald et al., "Immunohistochemical Localisation of Natriuretic Peptides in the Heart and Brain of the Gulf Toadfish *Opsanus beta*," Cell Tissue Res. 269:151-158, 1992.
Drewett et al., "The Family of Guanylyl Cyclase Receptors and Their Ligands," Endocrine Reviews 15:135-162, 1994.
Dzimiri et al. "Differential Regulation of Atrial and Brain Natriuretic Peptides and its Implications for the Management of Left Ventricular Volume Overload," Eur. J. Clin. Invest 32:563-569, 2002.

(Continued)

*Primary Examiner* — Shulamith H Shafer
(74) *Attorney, Agent, or Firm* — Clark & Elbing LLP

(57) ABSTRACT

An in vitro method of determining activation or inactivation of the atrial natriuretic peptide (ANP) and brain natriuretic peptide (BNP) hormonal systems, the method comprising simultaneously detecting the presence or amount of atrial and brain natriuretic peptide prohormones (proANP and proBNP) or fragments thereof in a sample.

20 Claims, 5 Drawing Sheets

OTHER PUBLICATIONS

Hasegawa et al., "Light and Electron Microscopic Localization of Brain Natriuretic Peptide in Relation to Atrial Natriuretic Peptide in Porcine Atrium," Circulation 84:1203-1209, 1991.

Hira et al., "Immunoactive Iso-ANP/BNP in Plasma, Tissues and Atrial Granules of the Rat," Regulatory Peptides 44: 1-9, 1993.

Kannel et al., "Changing Epidemiological Features of Cardiac Failure," Br. Heart J. 72 (Supplement):3-9, 1994.

Kohse et al., "Quantitative Determination of Natriuretic Peptides in Human Biological Samples with a Bioassay Using Cultured Cells," Eur. J. Clin. Chem. Clin. Biochem. 30: 837-845, 1992.

Mair et al., "The Impact of Cardiac Natriuretic Peptide Determination on the Diagnosis and Management of Heart Failure," Clin. Chem. Lab Med. 39:571-588, 2001.

Masson et al., "Comparative Measurement of N-Terminal Pro-Brain Natriuretic Peptide and Brain Natriuretic Peptide in Ambulatory Patients with Heart Failure," Clin. Chem. Lab Med. 40:761-763, 2002.

McDonagh et al., "Symptomatic and Asymptomatic Left-Ventricular Systolic Dysfunction in an Urban Population," Lancet 350:829-833, 1997.

Omland et al., "N-Terminal Pro-B-Type Natriuretic Peptide and Long-Term Mortality in Acute in Coronary Syndromes," Circulation 106:2913-2918, 2002.

Remes et al., "Validity of Clinical Diagnosis of Heart Failure in Primary Health Care," Eur. Heart J. 12:315-321, 1991.

Sagnella, "Measurement and Significance of Circulating Natriuretic Peptides in Cardiovascular Diseases," Clin. Sci. 95:519-529, 1998.

Struthers, "Ten Years of Natriuretic Peptide Research; a New Dawn for their Diagnostic and Therapeutic Use," BMJ 308:1615-1619, 1994.

Takemura et al., "Expression of Atrial and Brain Natriuretic Peptides and Their Genes in Hearts of Patients with Cardiac Amyloidosis," JACC 31: 254-265, 1998.

Talwar et al., "Towards a Blood Test for Heart Failure: the Potential Use of Circulating Natriuretic Peptides," Br. J. Clin. Pharmacol. 50:15-20, 2000.

Troughton et al., "Treatment of Heart Failure Guided by Plasma Aminoterminal Brain Natriuretic Peptide (N-BNP) Concentrations," Lancet 355:1126-1130, 2000.

Wilkins et al., "The Natriuretic-Peptide Family," Lancet 349:1307-1310, 1997.

Yasue et al., "Localization and Mechanism of Secretion of B-Type Natriuretic Peptide in Comparison with those of A-Type Natriuretic Peptide in Normal Subjects and Patients with Heart Failure," Circulation 90:195-203, 1994.

Yoshimura M et al., "Different Secretion Patterns of Atrial Natriuretic Peptide and Brain Natriuretic Peptide in Patients with Congestive Heart Failure," Circulation 87:464-469, 1993.

International Preliminary Report on Patentability for PCT/EP2004/006971.

Misono et al., "Expression and Purification of the Extracellular Ligand-binding Domain of the Atrial Natriuretic Peptide (ANP) Receptor: Monovalent Binding with ANP Induces 2:2 Complexes," Biochem. 38:516-523, 1999.

Nishikimi et al., "Increased Plasma Levels of Adrenomedullin in Patients with Heart Failure," JACC 26:1424-1431, 1995.

Qi et al., "Natriuretic Peptides in Patients with Aortic Stenosis," American Heart Journal 142:725-732, 2001.

Ruskoaho, "Cardiac Hormones as Diagnostic Tools in Heart Failure," Endocr. Rev. 24:341-356, 2003.

Squire et al., "N-Terminal Pro-Atrial Natriuretic Peptide (N-ANP) and N-Terminal Pro-B-Type Natriuretic Peptide (N-BNP) in the Prediction of Death and Heart Failure in Unselected Patients Following Acute Myocardial Infarction," Clin. Sci. 107:309-316, 2004.

* cited by examiner

|  | Echo CO change | NT-ProANP change | NT-ProBNP change | NT-ProXNP change |
|---|---|---|---|---|
| Cut-off | > +10% | > -20% | > -20% | > -20% |
| Positive | 9 | 9 | 9 | 11 |
| Negative | 2 | 2 | 2 | 0 |
| Sensitivity | 81.8 | 81.8 | 81.8 | 100.0 |

# METHODS OF DETERMINATION OF ACTIVATION OR INACTIVATION OF ATRIAL NATRIURETIC PEPTIDE (ANP) AND BRAIN NATRIURETIC PEPTIDE (BNP) HORMONAL SYSTEMS

CROSS-REFERENCE TO RELATED APPLICATIONS

This application claims priority under 35 U.S.C. §371 from international application PCT/EP2004/006971, filed Jun. 28, 2004, which claims priority from United Kingdom Application Serial No. 0315291.5, filed Jun. 30, 2003.

TECHNICAL FILED OF THE INVENTION

The invention relates to test methods useful for the diagnosis and/or monitoring treatment of cardiac conditions such as heart failure and to substances for use in the methods.

BACKGROUND OF THE INVENTION

Congestive heart failure (CHF) is a clinical syndrome caused by heart disease, characterised by breathlessness and abnormal sodium and water retention, and resulting in oedema. This occurs when the heart is unable to generate a cardiac output sufficient to meet the demands of the body without marked increase of diastolic pressure. It is a consequence of a cardiac disease which impairs ventricular systolic or diastolic function, or both. It is not a single disease but the end stage of many different forms of heart diseases, the most common of which are the coronary artery diseases, hypertension and diabetes (Kannel et al. 1994). Heart failure is manifested by symptoms of poor tissue perfusion (e.g., fatigue, poor exercise tolerance) or congestion of vascular beds (e.g., dyspnoea, pulmonary oedema, peripheral oedema) or both. Treatment of heart failure is generally directed towards its underlying causes.

The prevalence of symptomatic heart failure in the general population in Europe is estimated to be about 0.4-2%. As the prevalence rises rapidly with age, the increasing life expectancy is expected to have a major impact on the incidence of heart failure in the near future. The asymptomatic form of left-ventricular systolic dysfunction is estimated to be as common as symptomatic congestive heart failure (McDonagh et al. 1997).

The current routine clinical and investigative parameters used for the diagnosis of heart failure (clinical examination, electrocardiography, chest X-ray) have been found to be inadequate because the diagnosis causes false-positive results (Remes et al. 1991). Echocardiography provides specific diagnostic and prognostic information, but it is not particularly suitable for screening or for rapid point-of-care diagnostics. Thus, there is a need for new diagnostic tests for cardiac impairment.

A number of studies have demonstrated the usefulness of measurement of single peptides derived from atrial natriuretic peptide prohormone (proANP) and brain natriuretic peptide prohormone (proBNP) in the diagnosis of heart failure (Talwar et al. 2000; De Lemos et al. 2001; Daly et al. 2002). Cardiac impairment is associated with elevated circulating levels of atrial natriuretic peptide (ANP), brain natriuretic peptide (BNP), N-terminal fragment of proANP (NT-proANP) and N-terminal fragment of proBNP (NT-proBNP) (Sagnella 1998). High plasma concentrations correlate with poor prognosis after myocardial infarction and heart failure (Omland et al. 2002). Moreover, monitoring plasma levels of NT-proBNP appears to offer more powerful guidance in therapy of heart failure than follow-up by conventional clinical parameters (Troughton et al. 2000).

However prior art diagnostic methods, such as those disclosed in WO 87/06938, WO 00/35951, WO 91/00292, U.S. Pat. No. 5,786,163, EP 648 228 B1, WO 00/45176, WO 00/19207, U.S. Pat. No. 6,124,430, EP 542 255 B1) or those commercially available, are only intended to measure, and are only capable of measuring, a single peptide (ANP, BNP, NT-proANP or NT-proBNP) at a time. For example, the prior art discloses the use of ANP receptor or NPRA (GC-A) receptor in assays to determine natriuretic peptides, but does not disclose any simultaneous determination of natriuretic peptides. U.S. Pat. No. 5,747,274 discloses simultaneous detection of at least three cardiac markers using at least three different monoclonal or polyclonal antibody pairs, each specific for a different marker. Consequently, these assays produce multiple results. Thus there remains in the art a need for a reliable and sensitive but relatively cheap and simple means for detecting or diagnosing cardiac impairment such as heart failure.

Accordingly the present invention provides a test method which detects activation or inactivation of the ANP and BNP hormonal systems by assaying for both proANP- and proBNP-derived peptides simultaneously. Both proANP and proBNP derived peptides may be assayed in the same sample, at the same time. The method produces a single result and is simpler to perform than prior art methods. Moreover the present assay methods show greater sensitivity than prior art methods. Further still, the present test has a profound capability to give a reliable test result whether the patient is in an early phase or late phase of heart failure. The single assay format of the present invention, performed simultaneously per se, offers a cheaper and more cost effective alternative to the available tests thus allowing reliable measurement of activation or inactivation of both the ANP and the BNP hormonal systems

SUMMARY OF THE INVENTION

Accordingly the present invention provides an in vitro method of determining activation or inactivation of the atrial natriuretic peptide (ANP) and brain natriuretic peptide (BNP) hormonal systems, the method comprising simultaneously detecting the presence or amount of atrial and brain natriuretic peptide prohormones (proANP and proBNP) or fragments thereof in a sample.

The invention also provides:
an agent which comprises:
(a) (i) proANP (SEQ ID NO. 1), ANP (SEQ ID NO. 2) or NT-proANP (SEQ ID NO. 3);
   (ii) a homologous sequence having at least 70% identity to (i); or
   (iii) a fragment of (i) or (ii) which is at least 6 amino acids in length; and
(b) (i) pro-BNP (SEQ ID NO. 4), BNP (SEQ ID NO. 5), NT-proBNP (SEQ ID NO. 6);
   (ii) a homologous sequence having at least 70% identity to (i); or
   (iii) a fragment of (i) or (ii) which is at least 6 amino acids in length;
a polynucleotide comprising sequence which encodes the agent, or complementary sequence:
an expression vector and host cell comprising the polynucleotide;

a process for producing the polypeptide agent which comprises:
(a) cultivating the host cell under conditions to provide for expression of the polypeptide; and optionally
(b) recovering the expressed polypeptide;
a method of identifying a substance that binds specifically to
(a) (i) proANP (SEQ ID NO. 1), ANP (SEQ ID NO. 2) or NT-proANP (SEQ ID NO. 3);
(ii) a homologous sequence having at least 70% identity to (i); or
(iii) a fragment of (i) or (ii) which is at least 6 amino acids in length and
(b) (i) pro-BNP (SEQ ID NO. 4), BNP (SEQ ID NO. 5), NT-proBNP (SEQ ID NO. 6);
(ii) a homologous sequence having at least 70% identity to (i); or
(iii) a fragment of (i) or (ii) which is at least 6 amino acids in length which method comprises:
(A) contacting a candidate substance with (a) and (b) under conditions which allow specific binding; and
(B) determining whether the candidate substance binds to (a) and (b);
an antibody, fragment or derivative thereof which is able to bind to both:
(a) (i) proANP (SEQ ID NO. 1), ANP (SEQ ID NO. 2) or NT-proANP (SEQ ID NO. 3);
(ii) a homologous sequence having at least 70% identity to (i); or
(iii) a fragment of (i) or (ii) which is at least 6 amino acids in length; and
(b) (i) pro-BNP (SEQ ID NO. 4), BNP (SEQ ID NO. 5) or NT-proBNP (SEQ ID NO. 6);
(ii) a homologous sequence having at least 70% identity to (i); or
(iii) a fragment of (i) or (ii) which is at least 6 amino acids in length
a process for making the antibody;
a solid support comprising the antibody.

The invention further provides methods of diagnosing and/or monitoring treatment of heart failure and a diagnostic kit for use in such methods.

BRIEF DESCRIPTION OF THE SEQUENCES

Figure 1:
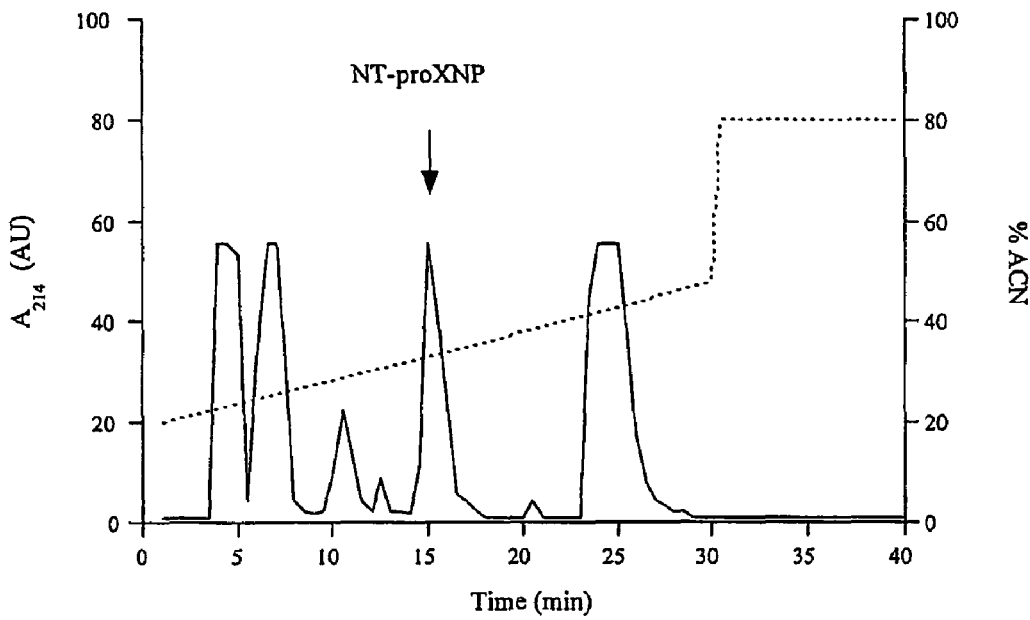
FIG. 1: Purification by reverse phase HPLC of a novel protein or peptide agent of the invention.

SEQ ID NO: 1 amino acid sequence of human proANP
SEQ ID NO: 2 amino acid sequence of human ANP
SEQ ID NO: 3 amino acid sequence of human NT-proANP
SEQ ID NO: 4 amino acid sequence of human proBNP
SEQ ID NO: 5 amino acid sequence of human BNP
SEQ ID NO: 6 amino acid sequence of human NT-proBNP
SEQ ID NO: 7 nucleotide sequence encoding human proANP
SEQ ID NO: 8 nucleotide sequence encoding human ANP
SEQ ID NO: 9 nucleotide sequence encoding human NT-proANP
SEQ ID NO: 10 nucleotide sequence encoding human proBNP
SEQ ID NO: 11 nucleotide sequence encoding human BNP
SEQ ID NO: 12 nucleotide sequence encoding human NT-proBNP
SEQ ID NO: 13 amino acid sequence of an agent according to the invention NT-proXNP1
SEQ ID NO: 14 amino acid sequence of an agent according to the invention NT-proXNP2
SEQ ID NO: 15 amino acid sequence of an agent according to the invention NT-proXNP3
SEQ ID NO: 16 amino acid spacer sequence
SEQ ID NO: 17 amino acid sequence of an agent according to the invention NT-proXNP4
SEQ ID NO: 18 amino acid sequence of an agent according to the invention NT-proXNP5
SEQ ID NO: 19 amino acid sequence of an agent according to the invention proXNP6
SEQ ID NO: 20: amino acid sequence of an agent according to the invention XNP7
SEQ ID NO: 21 nucleotide sequence encoding NT-proXNP1
SEQ ID NO: 22 nucleotide sequence encoding NT-proXNP2
SEQ ID NO: 23 nucleotide sequence encoding NT-proXNP3
SEQ ID NO: 24 nucleotide sequence encoding NT-proXNP4
SEQ ID NO: 25 nucleotide sequence encoding NT-proXNP5
SEQ ID NO: 26 nucleotide sequence encoding proXNP6
SEQ ID NO: 27 nucleotide sequence encoding XNP7
SEQ ID NO: 28 primer sequence
SEQ ID NO: 29 primer sequence
SEQ ID NO: 30 primer sequence
SEQ ID NO: 31 primer sequence
SEQ ID NO: 32 primer sequence
SEQ ID NO: 33 amino acid sequence of human GC-A receptor
SEQ ID NO: 34 amino acid sequence of extracellular domain of human GC-A receptor
SEQ ID NO: 35 amino acid sequence of human GC-B receptor
SEQ ID NO: 36 amino acid sequence of human GC-C receptor

DETAILED DESCRIPTION OF THE INVENTION

The present invention relates to a new test method which is useful for diagnosing and/or monitoring treatment of cardiac disease, in particular heart failure and to components and kits for use in the method. The method allows the detection of activation or inactivation of the atrial natriuretic peptide (ANP) hormonal system and the brain natriuretic peptide (BNP) hormonal system in an individual simultaneously. A single-test method may be used. In general the method assays simultaneously for the presence and/or amount of peptides derived from A- and B-type natriuretic peptide prohormones in a suitable biological sample obtained from the individual.

TERMS AND ABBREVIATIONS proANP is atrial natriuretic peptide prohormone;
proANP is processed by cleavage of the N-terminal fragment into the mature atrial natriuretic peptide (ANP). Human proANP has 126 amino acids (proANP$_{1-126}$)

```
                                          SEQ ID NO: 1
NPMYNAVSNA DLMDFKNLLD HLEEKMPLED EVVPPQVLSE

PNEEAGAALS PLPEVPPWTG EVSPAQRDGG ALGRGPWDSS

DRSALLKSKL RALLTAPRSL RRSSCFGGRM DRIGAQSGLG

CNSFRY
```

ANP is atrial natriuretic peptide
Human ANP is formed by amino acids 99 to 126 of the prohormone (proANP$_{99-126}$)

```
                                          SEQ ID NO: 2
     SLRRSSCFGG RLMDRIGAQSG LGCNSFRY
```

NT-proANP is the N-terminal fragment of proANP
The N-terminal fragment of human proANP is formed by amino acids 1 to 98 (proANP$_{1-98}$)

```
                                          SEQ ID NO: 3
NPMYNAVSNA DLMDFKNLLD HLEEKMPLED EVVPPQVLSE

PNEEAGAALS PLPEVPPWTG EVSPAQRDGG ALGRGPWDSS

DRSALLKSKL RALLTAPR
```

ProBNP is brain natriuretic peptide prohormone,
proBNP is processed by cleavage of the N-terminal fragment into the mature brain natriuretic peptide (BNP). Human proBNP has 108 amino acids (proBNP$_{1-108}$)

```
                                          SEQ ID NO: 4
HPLGSPGSAS DLETSGLQEQ RNHLQGKLSE LQVEQTSLEP

LQESPRPTGV WKSREVATEG IRGHRKMVLY TLRAPRSPKM

VQGSGCFGRK MDRISSSSGL GGKVLRRH
```

BNP is brain natriuretic peptide
Human BNP is formed by amino acids 77 to 108 of the prohormone (proBNP$_{77-108}$)

```
                                          SEQ ID NO: 5
     SPKMVQGSGC FGRKMDRISS SSGLGCKVLR RH
```

NT-proBNP is the N-terminal fragment of proBNP
The N-terminal fragment of human proBNP is formed by amino acids 1 to 76 (proBNP$_{1-76}$)

```
                                          SEQ ID NO: 6
HPLGSPGSAS DLETSGLQEQ RNHLQGKLSE LQVEQTSLEP

LQESPRPTGV WKSREVATEG IRGHRKMVLY TLRAPR
``` proXNP is an agent of the invention which comprises amino acid sequence derived or originating from both proANP and proBNP XNP is an agent of the invention which comprises amino acid sequence derived or originating from both ANP and BNP
NT-proXNP is an agent of the invention which comprises amino acid sequence derived or originating from both NT-proANP and NT-proBNP
NT-proXNP1 is an agent of the invention formed from proBNP$_{15-24}$ and proANP$_{82-96}$
NT-proXNP2 is an agent of the invention formed from proBNP$_{1-37}$ and proANP$_{29-98}$
NT-proXNP3 is an agent of the invention formed from proBNP$_{10-29}$ and proANP$_{20-80}$
NT-proXNP4 is an agent of the invention formed from proBNP$_{1-76}$ and proANP$_{1-98}$
NT-proXNP5 is an agent of the invention formed from proBNP$_{10-29}$ and proANP$_{60-80}$
ProXNP6 is an agent of the invention formed from proBNP$_{1-108}$ or a subsequence thereof and proANP$_{1-126}$ or a subsequence thereof
XNP7 is an agent of the invention formed from proBNP$_{77-92}$ or a subsequence thereof and proANP$_{112-126}$ or a subsequence thereof.

Variant Polypeptides

Variants of polypeptides are referred to herein. For example, references are made to variants of proANP, ANP, NT-proANP, proBNP, BNP and NT-proBNP, in the description of binding substances and agents of the invention. Reference is also made to variants of the GC-A, GC-B and GC-C receptor polypeptides.

The term "variant" refers to a polypeptide which has the same essential character as or a basic biological functionality of the relevant polypeptide. Thus a variant is typically capable of complementing one or more activities of that polypeptide. Typically a variant comprises an amino acid sequence which is homologous to all or a part of the sequence of the polypeptide. In general a (homologous) variant has an amino acid sequence with more than 70% identity, preferably at least 75% or 80% or at least 90% and particularly preferably at least 95%, at least 97% or at least 99% identity with the given sequence, for example over a region of at least 15, 20, 30, 40, 50, 60, 70, 80, 90, 100, 200, 300, 400 or more contiguous amino acids. Variants may include allelic variants, species homologues and the deletion, modification or addition of single amino acids or groups of amino acids within the protein sequence, as long as the peptide maintains a basic biological functionality of the subject polypeptide.

An allelic variant will be a variant which will occur naturally, for example, in a human, and which will function in a substantially similar manner to the relevant polypeptide. Similarly, a species homologue of a protein will be the equivalent protein which occurs naturally in another species and which retains a basic biological function of the given polypeptide. Thus, for example, a naturally occurring or native polypeptide variant, such as those which may be detected in a biological sample, may be an allelic variant or species homologue of another known polypeptide.

Allelic variants and species homologues can be obtained, for example, by probing a library made from cells of the appropriate species using a suitable probe, to obtain clones encoding the allelic or species variants. The clones can be manipulated by conventional techniques to generate a polypeptide which can be produced by recombinant or synthetic techniques known per se.

Variants may include polypeptides which are longer in length than the relevant polypeptide. A variant may comprise or consist of at least 30, 40, 50, 60, 70, 80, 90, 100, 150, 200, 300, 400, amino acids up to for example 500, 1000 or 2000 amino acids.

A variant may be a fusion protein.

Variants may include amino acid substitutions, for example from 1, 2 or 3 to 10, 20 or 30 (or 10, 20, 30 or 40 to 50, 60 or 70) substitutions. The modified polypeptide generally retains the ability to complement one or more of the activities of and/or the antigenic activity of the subject polypeptide. Conservative substitutions may be made, for example according to the following table. Amino acids in the same block of the second column and preferably in the same line in the third column may be substituted for each other.

|  | | |
|---|---|---|
| ALIPHATIC | Non-Polar | G A P |
| | | I L V |
| | Polar-uncharged | C S T M |
| | | N Q |
| | Polar-charged | D E |
| | | K R |
| AROMATIC | | H F W Y |

Shorter polypeptide sequences or fragments are within the scope of the invention. For example, a peptide of at least 2, 5, 10, 12, 15, 17, 20, 25 amino acids or up to 30, 40, 50, 60, 70, 80, 100, 200, 300, 400 or 500 amino acids in length (depending on the size of the subject polypeptide) is considered to fall within the scope of the invention as long as it demonstrates a basic biological functionality of the subject polypeptide. In particular, but not exclusively, this aspect of the invention encompasses the situation when the protein is a fragment of the complete protein sequence and may represent a binding site for another molecule or entity, such as a peptide-binding region, or an epitope. Such fragments may or may not retain other functions of the subject polypeptide.

Variant polypeptides as referred to herein generally retain a basic biological functionality of the relevant polypeptide. The variant may retain one or more of the native biological activities or functions of the subject polypeptide.

In particular, a variant as referred to herein generally retains one or more of the binding characteristics of the relevant polypeptide. Alternatively or additionally, the variant may retain an antigenic activity of the polypeptide.

In one embodiment a variant exhibits at least one of the binding or recognition properties of the subject polypeptide. In particular a variant may be capable of binding to a product that can bind to the polypeptide e.g. a ligand, a receptor or an antibody. Thus, for example, a variant of ANP or BNP may be capable of binding to the GC-A receptor. Similarly, a variant of the GC-A or GC-B receptor may bind ANP or BNP. Typically a variant binds the product with an affinity that is at least 60%, such as at least 70, 80 or 90%, for example 95, 97 or 99% of the affinity with which the relevant polypeptide binds to the product. Suitable binding assays are known in the art.

Variants which have a particular activity or binding characteristic of the given polypeptide may be identified based on such activities or characteristics, for example from a library of polypeptides.

In a further embodiment a variant polypeptide may retain the antigenic properties of the subject polypeptide. Such a variant may, for example, be capable of generating an immune response in a subject. The immune response may be antibody and/or cell mediated, such as T-cell mediated. Thus a variant may be capable of raising antibodies which are specific for and bind to the subject polypeptide. A peptide for generating an immune response may be identified by immunisation studies, typically in an animal model. For example, a candidate peptide may be administered to an animal and subsequently the antibody or T-cell response generated which is specific for the peptide may be determined. Antiserum generated following administration of a peptide to an animal may be evaluated for the ability to bind the peptide or to bind the subject polypeptide.

A variant which has at least one of the binding characteristics of a given polypeptide may comprise at least one binding region of the polypeptide. Such a binding region in general mediates binding of the polypeptide to another product such as a receptor or an antibody. The binding region may be external or internal to the given polypeptide. Thus a variant may comprise a binding site, epitope or antigenic fragment of the relevant polypeptide. Preferably the binding region in the variant retains the conformation which it has in the relevant polypeptide. In one aspect the variants are fragments. For example the fragments may be at least 6 amino acids in length, preferably at least 10, such as at least 12 or 15 or up to 20, 30 or 40 amino acids. Longer fragments such as up to 60, 90, 100 or 200 amino acids may also be used. Such fragments may not otherwise demonstrate a cellular function or activity of the subject polypeptide.

ANP and BNP

Cardiac natriuretic peptides ANP and BNP and the N-terminal fragments (NT-proANP and NT-proBNP) of A- and B-type natriuretic peptide prohormones (proANP and proBNP) are released to the circulation when the heart is subjected to pressure or volume overload. Their function is to decrease the load and protect the heart. In spite of the fact that the heart produces two distinct biologically active natriuretic peptides (ANP and BNP), each derived from its own gene and regulated differently, their biological effects are mediated to the target cells by a single receptor, GC-A (NPRA) (Drewett et al. 1994). Activation of both the ANP and BNP hormonal systems refers to the up-regulation of both ANP and BNP genes or production or increase in plasma concentrations, whereas inactivation of both ANP and BNP systems refers to the down-regulation of both ANP and BNP genes or production or decrease in plasma concentration.

In cardiac pressure and volume overload, ANP gene expression and the circulating levels of ANP and NT-proANP are primarily induced by increased preload of the heart, whereas BNP gene expression and circulating levels of BNP and NT-proBNP are primarily sensitive to an increase of afterload (Yoshimura et al. 1993; Yasue et al. 1994). Moreover, ANP and BNP genes are regulated differentially in the different chambers of the heart (Dzimiri et al. 2002). Elevated plasma ANP or NT-proANP levels are associated with atrial overload e.g. tachycardia, whereas BNP and NT-proBNP are, better markers of ventricular overload e.g. aortic stenosis. Markedly elevated circulating levels of both ANP and BNP (and NT-proANP and NT-proBNP) suggest combined atrial and ventricular overload, as in dilated cardiomyopathy. Thus, in physiological and pathophysiological situations the information mediated by ANP and BNP converges in the target cell membrane to cause a common intracellular signalling cascade. As already mentioned existing assays measure one of the analytes at a time (ANP, BNP, NT-proANP or NT-proBNP). Because a major strength of the natriuretic peptides in the diagnosis of cardiac diseases lies in the high negative predictive value, the combination assay of ANP and BNP (or NT-proANP and NT-proBNP) in the present invention will add value over that provided by assaying any of the analytes alone. Sequential assay of ANP and BNP (or NT-proANP and NT-proBNP) would be unnecessarily complex, including doubled effort for quality control, and not as cost-effective.

The present invention provides novel diagnostic methods and use thereof which, by mimicking the physiological regulatory system working in the body, can combine the information obtained from the activation or inactivation, respectively, of the ANP and the BNP hormonal systems by a simple means of simultaneous measurement of a proportionally cumulative concentration of peptides derived from both A- and B-type natriuretic peptide prohormones.

Test Methods

The invention provides a new and sensitive method suitable for diagnosing and assessing cardiac conditions such as heart failure, which determines activation or inactivation of the ANP and BNP hormonal systems. The method of the invention focuses on detecting or monitoring the combined levels of proANP, proBNP and fragments thereof in a suitable biological sample. According to the method, peptides derived from or originating from both proANP and proBNP may be assayed at the same time in a given sample. In one embodiment the method may be used for screening for diagnostic purposes or for monitoring treatment.

Peptides derived from proANP and proBNP include NT-proANP, ANP, NT-proBNP, BNP as well as proANP and proBNP. The sample may comprise other peptides also derived from the prohormones eg by proteolysis. For example, other peptides may include $proANP_{1-30}$ $proANP_{31-67}$ or $proANP_{79-98}$. Thus in one embodiment, any combination of proANP, NT-proANP, ANP, proBNP, NT-proBNP and BNP, and optionally other derived peptides, may be assayed in the method. In one embodiment the sample may contain proANP-derived peptides without proBNP-derived peptides or vice versa.

Since the peptides are detected simultaneously, only a single reading or result is required. The method is suitable for assessing the risk of and detecting cardiac impairment such as heart failure, and for evaluating treatments for heart failure. As such it is more sensitive, cheaper and simpler to perform than prior art methods.

The peptides assayed in the invention are present at normal reference levels in the general population. Activation of the ANP and BNP systems may be considered as occurring when the combined peptide level is greater than this normal reference level. Therefore in any particular assay format, if the result indicates a qualitatively or quantitatively higher peptide level than the reference level, activation of the systems is implied. For example, an assay may be calibrated eg using an agent of the invention, so that a particular reading in the assay is known to represent the normal peptide level. Or the assay may be such that a normal or reference level of peptide will produce a negligible or insignificant result.

Inactivation of the ANP and BNP systems, for example after heart failure perhaps in response to medical treatment, occurs when the combined peptide level falls from the elevated level associated with the earlier cardiac incident. By performing serial assays it will be possible to detect a qualitative or quantitative decrease in peptide levels. It will be possible to determine also the rate of decrease and so to assess the effectiveness of a given treatment.

The present methods are capable of simultaneously detecting both proANP-derived and proBNP-derived peptides. The actual change in individual peptide levels may be for example A+ and B+, A+ and B−, A− and B+, or A− and B− (where A represents levels of proANP-derived peptides and B represents levels of proBNP-derived peptides).

The present assay methods may be qualitative or quantitative. For example, a quantitative assay is possible when an agent of the invention is used as a competing antigen in a competition assay.

In general, the present method comprises contacting a sample with a first binding substance which is able to bind both proANP- and proBNP-derived peptides under conditions which will allow such binding to occur. Any binding complexes formed between the first binding substance and such peptides are then detected. Suitable detection means are known in the art and are described in more detail below.

The peptides to be detected are as described above. In one aspect they are naturally occurring peptides. The peptides provide an indicator of activation or inactivation of the ANP and BNP systems. The first binding substance is as defined herein.

In one embodiment the first binding substance is a bi- or oligo-specific binding substance as defined herein. Such a binding substance is able to bind to both proANP- and proBNP-derived peptides. In one embodiment this first binding substance is used in the assay when an agent of the invention is not used in the assay, for example as a competing antigen in a competitive binding assay. Binding complexes between the first binding substance and the peptides in the sample may be detected and activation or inactivation determined as above.

In one aspect, the present method additionally comprises contacting a sample with an agent of the invention as described herein (XNP, proXNP, or NT-proXNP). The agent comprises peptides derived from or originating from both proANP and proBNP and is able to bind to the first binding substance. Such an agent may be used as a standard to calibrate the present assays. The agent may be used as a competing antigen in a competition assay. Peptide levels in a given sample may thus be expressed in terms of agent concentration. Suitable assay formats, detection and quantifying means are known in the art and are described in more detail below.

The methods of the invention are generally applied to a sample, typically a biological sample. Typically the sample is one which is known or suspected of being a body sample from an individual, such as a human. A sample may be one taken from an individual or patient. The sample may comprise a body fluid, e.g. blood, serum, plasma, cerebrospinal fluid, urine, saliva or other biological fluid in which peptides derived from A- and B-type natriuretic peptide prohormones might be present. The sample may be a human sample. In one embodiment the sample is obtainable from an individual or patient using a standard or routine procedure. The sample may therefore be such that the assay can be used for diagnostic screening or therapeutic monitoring or assessment. In one aspect the sample is obtainable from a living individual or subject.

A sample may be processed before it is used in the method. For example, it may be diluted, typically in water, saline or saline containing a buffer (any of these diluents may additionally comprise detergent).

Generally, the present method is carried out in aqueous solution. However, in particular embodiments (some of which are discussed below), the first binding substance, or the agent may be immobilised in a solid support. Typically such a support is the surface of the container in which the method is being carried out, such as the surface of a well of a microtitre plate. In other embodiments the support may be a sheet (e.g. a nitrocellulose or nylon sheet) or a bead (e.g. sepharose or latex).

In one embodiment the solid support is a particle, dipstick or microtitre plate. An ELISA plate may be used.

The first binding substance or the agent may be labelled with a detectable label. Examples of suitable labels have been described herein.

In principle, any suitable assay technique may be employed in the present invention. For example, suitable methods include immunoassay methods, both competitive and non-competitive, antibody binding methods employing either unlabelled or labelled antigens or their analogues (immunoassays), or labelled or unlabelled binding substances recognising their antigens or analogues (immunometric assays and receptor binding assays), respectively. Sandwich assays may be used.

Immunoassay methods which may be used include europium fluorescence immunoassays (FIA), enzymelinked immunoabsorbent assays (ELISA), radioimmunoassay (RIA), immunoradiometric assay, enzyme immunoassay, immunoenzymometric assay, time-resolved fluoroimmunoassay, immunofluorometric assay, chemiluminescence immunoassay (CLIA), anodic or cathodic electrochemiluminescence immunoassays, various dry-chemistry test strip assays, particle based immunoassays, direct labelless immunoassays, such as assays based on surface plasmon resonance, surface acoustic waves and surface-enhanced Raman spectroscopy, homogeneic immunoassays such as proximity assays with two different labels, chip technology, array technology, particle enhanced immunoassays and other particle immunoassays, both single and dual size labelled or unlabelled particles. Latex and gold, in different forms, can be mentioned as examples of particles to be used. Turbidometric and nephelometric determinations are also possible assay formats.

Chromatographic membrane technology can also be used as a format to implement the present invention. The chromatographic membrane test comprises both a lateral and flow-through test. The used reagents are either permanently or non-permanently immobilised onto the membrane where they have a very distinct role in the different zones of the test i.e. one or multiple zone(s) for reagent(s), test(s), control(s) etc. The reagents immobilised can be binding substance, the agent of the invention, anti-binding substance antibody, anti-analyte antibody, anti-agent antibody or a label.

Binding complexes of the first binding substance with peptides in the sample or with the agent may be detected using a second binding substance. For example, the second binding substance may be an antibody which itself bears a detectable label such as those listed above. The second binding substance may be a substance that causes precipitation or otherwise immobilises and separates the first binding substance complexes.

Particular embodiments of the present method will now be described in more detail:

(a) One embodiment uses labelled proXNP agent as antigen, together with antibody as first binding substance recognising both peptides derived from both A- and B-type natriuretic peptide prohormones and the agent. In such methods a known constant amount of labelled agent is added to the sample containing an unknown amount of unlabelled antigen, i.e. peptide analyte to be measured. Both the labelled and the unlabelled antigen bind to the first binding substance, for example in a competitive manner and measurement of the amount of the bound labelled agent, when compared to the known amount agent added, can be used to determine how much unlabelled antigen is present in the sample thus reflecting the activation or the inactivation of both the ANP and the BNP systems as a proportionally cumulative measure of peptides derived from both A- and B-type natriuretic peptide prohormones.

(b) Another preferred type of method uses a labelled first binding substance. In such methods, the complex of labelled first binding substance and peptides derived from both A- and B-type natriuretic peptide prohormones is assayed giving a proportionally cumulative measure of the amount of peptides derived from both A- and B-type natriuretic peptide prohormones in the sample. A specific case is the one where the first binding substance can be the natriuretic receptor GC-A or a fragment or extension thereof, a bi-, oligospecific or bifunctional antibody recognising peptides derived from both A- and B-type natriuretic peptide prohormones and agent.

(c) An additional type of method relies on the use of a labelled antibody to binding substance, which antibody may be produced in a different animal species than the used first or secondary antibody in case of binding substance comprising an antibody.

(d) A further method comprises (i) contacting the sample with an agent and a first binding substance, comprising labelled first binding substance or comprising labelled agent; and (ii) detecting and/or quantitatively determining the binding of the labelled first binding substance to the unlabelled agent or labelled agent to the binding substance that recognises peptides derived from both A- and B-type natriuretic peptide prohormones and agent.

(e) One method comprises contacting a sample, which sample is known or suspected to contain peptides derived from both A- and B-type natriuretic peptide prohormones with (in any order): (i) a first binding substance which recognises both peptides derived from both A- and B-type natriuretic peptide prohormones and an agent of the invention; and (ii) a known amount of the labelled agent, which acts as an antigen, such that the label is bound to the binding substance in an amount which depends on the amount of unlabelled peptides derived from both A- and B-type natriuretic peptide prohormones present in the sample; and assaying the amount of the bound and/or unbound label as a proportionally cumulative measure of unlabelled level of peptides derived from both A- and B-type natriuretic peptide prohormones in the sample.

(f) A conventional immunoassay method (e.g. radioimmunoassay) may comprise:
  (i) immobilising on a solid support unlabelled first binding substance recognising and binding peptides derived from both A- and B-type natriuretic peptide prohormones and agent of the invention;
  (ii) adding a sample containing or suspected of containing the target native peptides derived from both A- and B-type natriuretic peptide prohormones together with a fixed amount of labelled agent, such that the peptides derived from both A- and B-type natriuretic peptide prohormones and the labelled agent are free to compete for binding to the immobilised binding substance;
  (iii) separating out the immobilised (bound) material from the non-immobilised (unbound) material;
  (iv) determining the amount of binding substance-bound labelled agent; and
  (v) comparing the amounts of bound or unbound labelled agent in assay mixtures of test samples with the signal obtained using calibrators with known concentration of agent in order to determine the proportionally cumulative concentration of peptides derived from both A- and B-type natriuretic peptide prohormones in the sample being assayed.

(g) Alternatively, method (f) can be performed in solution, wherein, a second binding substance can be used to either precipitate or otherwise immobilise and separate the first binding substance-antigen complexes. A typical example of this comprises:
  (i) contacting a sample containing or suspected of containing the peptides derived from A- and B-type natriuretic peptide prohormones to be detected with a first binding substance recognising peptides derived from both A- and B-type natriuretic peptide prohormones or binding thereto according to the invention in the presence of a fixed amount of a labelled agent of the invention;
(ii) contacting the resulting mixture with an immobilised secondary binding substance which binds to the first binding substance;
(iii) separating out the immobilised material from the non-immobilised material; and
(iv) comparing amounts of the labelled agent in the immobilised or non-immobilised material with the amounts obtained using calibrators with known concentration of novel agent to determine the proportionally cumulative concentration of peptides derived from both A- and B-type natriuretic peptide prohormones in the sample being assayed.

(h) An immunometric assay employing the use of immobilised unlabelled agent is also envisioned, a typical example of which comprises:
(i) immobilising on a solid support unlabelled agent of the invention;
(ii) adding a sample containing or suspected of containing the target peptides derived from A- and B-type natriuretic peptide prohormones together with a fixed amount of labelled binding substance which recognises peptides derived from both A- and B-type natriuretic peptide prohormones according to the invention, in such a way that peptides derived from both A- and B-type natriuretic peptide prohormones in the sample are free to compete with the immobilised agent of the invention for the labelled binding substance.
(iii) separating out the labelled first binding substance recognising peptides derived from both A- and B-type natriuretic peptide prohormones that is not bound to the immobilised agent of the invention;
(iv) determining the amount of labelled binding substance bound to the immobilised agent of the invention; and
(v) comparing the amounts of immobilised or non-immobilised labelled binding substance in the assay mixtures of test samples with the activity obtained using calibrators with known concentration of agent of the invention, in order to determine the proportionally cumulative concentration of peptides derived from both A- and B-type natriuretic peptide prohormones in the sample being assayed.

Thus the invention provides methods for determination of the proportionally cumulative concentration of peptides derived from both A- and B-type natriuretic peptide prohormones in a sample, showing either an activation or inactivation of both the ANP and BNP systems.

The First Binding Substance

According to the present method, peptides derived from both proANP and proBNP may be assayed at the same time in a given sample. As above peptides derived from proANP and proBNP include NT-proANP, ANP, NT-proBNP, BNP as well as proANP and proBNP. A sample may comprise other peptides also derived from the prohormones eg by proteolysis. For example, other peptides may include proANP$_{1-30}$, proANP$_{31-67}$ or proANP$_{79-98}$. Thus in one embodiment, any combination of proANP, NT-proANP, ANP, proBNP, NT-proBNP and BNP, and optionally other derived peptides, may be assayed in the method.

The present assays use a first binding substance which recognises or binds to peptides derived from both A- and B-type natriuretic peptide prohormones, such as those peptides described above. Thus the substance is able to bind to both proANP and proBNP or to variants, including fragments of both prohormones. In one embodiment the first binding substance may not bind both sets of peptides with equal affinity. The binding substance may bind to naturally occurring proANP, ANP or NT-proANP and/or to naturally occurring proBNP, BNP, or NT-proBNP. For example it may bind to SEQ ID Nos 1, 2 or 3 and SEQ ID Nos 4, 5 or 6, or to allelic variants or species homologues thereof. Alternatively or additionally, the substance may bind to one or more fragments of any of the above sequences, for example fragments which include an epitope, antigenic fragment, or a binding site. Such fragments are discussed in more detail herein.

In one aspect the first binding substance is able to bind to both:
(a) (i) proANP (SEQ ID NO. 1), ANP (SEQ ID NO. 2) or NT-proANP (SEQ ID NO. 3);
  (ii) a homologous variant of (i); or
  (iii) a fragment of (i) or (ii);
and
(b) (i) pro-BNP (SEQ ID NO. 4), BNP (SEQ ID NO. 5) or NT-proBNP (SEQ ID NO. 6);
  (ii) a homologous variant of (i); or
  (iii) a fragment of (i) or (ii).

Variants and fragments are as defined herein.

In one embodiment, the homologous variant (ii) has at least 70% identity to (i), and/or the fragment (iii) is at least 6 amino acids in length. In one aspect the homologous variant (ii) is a species homologue or an allelic variant of (i).

In one embodiment a binding substance according to the invention is able to bind to a peptide comprising or consisting of amino acids 7 to 23 of ANP and/or amino acids 10 to 26 of BNP or variants thereof. These peptide regions form a conserved ring structure in the native molecules.

A binding substance may bind to an epitope of proANP and/or proBNP. For example, suitable epitopes include amino acids 5-13, 1-10, 15-25 and 27-32 of BNP and amino acids 65-76 and 1-13 of NT-proBNP or variants thereof In one embodiment, a binding substance is able to bind to one or more peptides selected from proBNP$_{1-37}$, proBNP$_{15-24}$, proBNP$_{10-29}$, proBNP$_{77-92}$, proBNP$_{1-108}$, proANP$_{29-98}$, proANP$_{82-96}$, proANP$_{20-80}$, proANP$_{60-80}$, proANP$_{1-126}$ and proANP$_{112-126}$ or variants thereof. For example, a binding substance may be able to bind to both proBNP$_{15-24}$ and proANP$_{82-96}$, to both proBNP$_{1-37}$ and proANP$_{29-98}$, to both proBNP$_{10-29}$ and proANP$_{20-80}$, to both proBNP$_{10-29}$ and proANP$_{60-80}$, to both proBNP$_{1-108}$ and proANP$_{1-126}$ or to both proBNP$_{77-92}$ and proANP$_{112-126}$. For example, a binding substance according to the invention may bind to NT-proXNP1 (SEQ ID NO:13), NT-proXNP2 (SEQ ID NO:14), NT-proXNP3 (SEQ ID NO:15) NT-proXNP4 (SEQ ID NO:17), NT-proXNP5 (SEQ ID NO: 18), proXNP6 (SEQ ID NO: 19) or XNP7 (SEQ ID NO: 20).

In those embodiments of the present invention which use a binding agent of the invention, the first binding substance is also able to bind to the binding agent.

Suitable binding assays for determining binding are known in the art. In general a first binding substance is able to bind a given peptide to an extent that it can be used in a binding and detection assay such as those described herein. For example, a suitable binding substance may bind with at least 50, 60, 70, 80, 90, 95 or 100% of the binding affinity of a specific antibody to the peptide, or of the natriuretic receptor GC-A to the peptide, e.g. of receptor GC-A to ANP or BNP.

The first binding substance as used herein may be a single substance or a mixture of substances. A suitable binding substance may be for example, a receptor or antibody, or fragments or derivatives thereof, with bi- or oligo-specific properties, or a mixture thereof.

In one aspect a mixture of binding substances is used as a first binding substance in embodiments where an agent of the invention is also used. A mixture may comprise monospecific, bispecific and/or oligospecific binding substances. Any suitable composition of binding substances may be used that allows detection of proANP- and proBNP-derived peptides according to the present methods. pro-ANP-derived peptide specific binding substances and proBNP-derived peptide specific binding substances may be present in any suitable proportions. For example they may be present in equal amounts or binding capacities. Alternatively, each may be present at, for example, 2×, 3×, 4×, 5× up to 10× the amount or binding capacity of the other. In one embodiment, a 1:1 mixture of proANP-derived peptide-specific binding substance eg antibody and proBNP-derived peptide specific binding substance eg antibody may be used in an assay.

In embodiments where the assay does not include agent of the invention it is preferred that the first binding substance is a single bi- or oligo-specific binding substance. Thus a first binding substance for use in such embodiments may be a single substance that is bi- or oligo-functional in binding. That single substance has the binding specificity of the first binding substance as set out above. It may for example, have two or more ligand binding sites, or two or more ligands may bind to one site in the substance with the same or different affinities. For example such a substance may comprise a receptor or antibody or fragments of either.

(a) Receptors

An example of a suitable receptor is natriuretic receptor GC-A. A sequence of human GC-A may be found under accession no. P16066 (SEQ ID NO:33). The receptor or a fragment, extension or derivative thereof can be produced by methods known to those skilled in the art (Misono et al., 1999). Briefly, the extracellular ligand binding domain of the receptor (SEQ ID NO:34) may be produced by cloning the DNA sequence encoding the amino acid sequence required for binding both human ANP and BNP, into a suitable prokaryotic or eukaryotic expression vector, transfecting the vector into an appropriate host cell, growing the host cell in a suitable culture medium, and harvesting the recombinant protein. The receptor-derived sequence may be released by enzyme digestion, purified with affinity chromatography and reverse-phase HPLC and identified by peptide mapping and sequencing.

The GC-B receptor (accession no. P20594, SEQ ID NO:35) or ANPrecC or clearance receptor (accession no. P17342, SEQ ID NO:36) may also act as a binding substance.

Thus in one embodiment the first binding substance may comprise:
(a) natriuretic receptor GC-A (SEQ ID NO: 33), GC-B (SEQ ID NO: 35) or GC-C (SEQ ID NO: 36);
(b) a homologous variant of (a); or
(c) a fragment of (a) or (b).

In one aspect the first binding substance comprises an extracellular binding domain of the natriuretic receptor GC-A (SEQ ID NO: 34) or a homologous variant of fragment thereof.

An extension or derivative of any of the above binding substances may be used. Thus the structure of the molecule may be modified, for example by adding a handle to facilitate attachment to a solid support, while still retaining the binding ability or properties of the molecule.

(b) Antibodies

The first binding substance may comprise an antibody or a fragment or derivative of an antibody. Thus in one aspect the present invention relates to antibody with the binding specificity set out above.

Antibodies may be raised against specific epitopes of the given peptide sequences. An antibody, or other compound, "specifically binds" to a polypeptide when it binds with preferential or high affinity to the protein or proteins for which it is specific but does substantially not bind or binds with only low affinity to other polypeptides. A variety of protocols for competitive binding or immunometric assays to determine the specific binding capability of an antibody are well known in the art (see for example Maddox et al, J. Exp. Med. 158, 1211-1226, 1993). Such immunoassays typically involve the formation of complexes between specific protein and antibody and the measurement of complex formation.

An antibody according to the invention may comprise either a whole antibody or a fragment thereof and has the binding specificity set out above. Fragments include Fv, F(ab') and F(ab')$_2$ fragments, as well as single chain antibodies. A whole antibody is typically an antibody which is produced by any of the methods of producing an antibody which are discussed herein. Typically the antibody is a mammalian antibody, such as a primate, human, rodent (e.g. mouse or rat), rabbit, ovine, porcine, equine, goat or camel antibody. The antibody can be any class or isotype of antibody, for example IgM, but is preferably IgG.

The antibody may be a bispecific antibody which is able to bind to two different antigens, or an oligospecific antibody which is able to bind to more than two different antigens. The antibody may comprise a polyclonal, monoclonal, oligoclonal, bifunctional or crossreacting polyclonal antibody as explained above.

A fragment of whole antibody that can be used in the method comprises an antigen binding site, e.g. F(ab') or F(ab)$_2$ fragments. Such fragments or antibodies may be used to form antibody derivatives. For example the whole antibody or fragment may be associated with other moieties, such as linkers which may be used to join together two or more fragments or antibodies. Such linkers may be chemical linkers or can be present in the form of a fusion protein with the fragment or whole antibody. The linkers may thus be used to join together whole antibodies or fragments which have the same or different binding specificities, e.g. that can bind the same or different polymorphisms. The antibody may be a "diabody" formed by joining two variable domains back to back. In one embodiment the antibody is a chimeric antibody comprising sequence from different natural antibodies, for example a humanised antibody. Bifunctional antibodies may be made by chemical combination of fragments with desired characteristics.

Antibodies of the invention can be produced by any suitable method. For example, antibodies, fragments or derivatives thereof may be produced by selecting immunogens to raise antibodies, chemically coupling antibodies or antibody fragments, somatic fusion of monoclonal hybridomas/splenocytes or recombinant techniques. Phage display techniques may be used in antibody production.

Means for preparing and characterising antibodies are well known in the art, see for example Harlow and Lane (1988) "Antibodies: A Laboratory Manual", Cold Spring Harbor Laboratory Press, Cold Spring Harbor, N.Y. For example, an antibody may be produced by raising antibody in a host animal against the whole polypeptide or a fragment thereof, for example an antigenic epitope thereof, or "immunogen". The fragment may be any of the fragments mentioned herein (typically at least 6 or at least 10 or 15 amino acids long). An agent of the invention may be used to raise antibody using known techniques.

A method for producing a polyclonal antibody comprises immunising a suitable host animal, for example an experimental animal, with the immunogen and isolating immunoglobulins from the animal's serum. The animal may therefore be inoculated with the immunogen, blood subsequently removed from the animal and the IgG fraction purified.

Polyclonal and monoclonal antibodies are produced by immunising a suitable host animal (e.g. rabbit, sheep, goat, swine, chicken, guinea pig, rat or mouse) with an immunogen. For example, the immunogen may comprise an agent according to the present invention. In one embodiment one or more boosters of immunogen are administered to the animal. For example, 1, 2, 3, 4 or more boosters may be used. Methods of producing polyclonal or monoclonal antibodies are well-known for those skilled in the art and any of these methods may be used to prepare antibodies. If desired, the immunogen may be administered as a conjugate, in which the immunogen is coupled, for example via a side chain of the amino acid residues to a suitable carrier. The carrier molecule is typically a physiologically acceptable carrier.

After the experimental animal has produced polyclonal antibodies the serum may be used diluted or the desired immunoglobulins may be isolated from the serum. In one embodiment the serum may be diluted before use. Suitable dilutions may include for example, from 1:1000 to 1:500,000, for example from 1:20,000 to 1:80,000, 1:10,000 to 1:15,000 or from 1:50,000 to 1:60,000. In one embodiment the concentration of antibody used in an assay of the invention is the same as the concentration of antibody in such a dilution of serum. The obtained antibody may be isolated and, if desired, purified, for example to a purity of 70%-100%. Typically the animal is inoculated with immunogen, the blood is removed and the IgG fraction is purified.

The methods for producing monoclonal antibodies are also well-known for those skilled in the art (Köhler & Millstein 1975 Nature 256, 495-497). Such methods generally comprise immortalising cells which produce the claimed antibody. Hybridoma cells producing monoclonal antibodies, are produced by fusing spleen cells from an immunised animal with tumour cells. The resulting hybridoma cells are immortalised and the cells produce the desired antibody. The immortalised cell producing the desired antibody may be selected by a conventional procedure. The hybridomas may be grown in culture or injected intraperitoneally, for formation of ascites fluid, or into the bloodstream of an allogeneic or immunocompromised host.

Human antibodies may be produced by in vitro immunisation of human lymphocytes, followed by transformation of the lymphocytes with Epstein-Barr virus. Monoclonal antibodies may also be produced by recombinant DNA technology as described by Skerra and Plückthun (1988). It is also possible to use any derivates, as for example F(ab'), and F(ab')$_2$ fragments of both monoclonal and polyclonal antibodies prepared by proteolytic reaction of papain and pepsin, respectively, on substantially intact antibodies by methods well known for a person skilled in the art.

Thus the antibodies provided by the invention (and those which are used in the method of the invention) may be made by culturing a cell that expresses the antibody and optionally purifying the antibody from the cell.

The cell used in the process may be one which is obtainable by administering a peptide comprising any of the relevant antigenic peptides to a mammal, extracting B cells from the mammal and selecting a cell from these based on the ability to express an antibody which binds the antigens. Optionally the B cells are immortalised after extraction or selection, for example by fusing them with an immortal cell (to form a hybridoma) or by infection with EBV virus.

Cells that express the antibody comprise a polynucleotide that is capable of expressing the antibody, a polynucleotide that encodes the antibody.

Another type of cell which can be used to make the antibody is one which is recombinant for a polynucleotide which expresses the antibody. Such a cell may be prokaryotic or eukaryotic (such as from any of the mammals mentioned herein).

Antibody may be immobilised on a solid support. Typically the solid support is the surface of the container in which the method is being carried out, such as the surface of a microtitre plate. In other embodiments the support may be a particle, a sheet (e.g. a nitrocellulose or nylon sheet) or a bead (e.g. Sepharose or latex). Antibody may be present on an ELISA plate or in a dipstick.

Antibodies of the invention are for example useful in purification, isolation or screening methods involving immunoprecipitation techniques.

The invention also includes a dipstick which can be used to carry out the method of the invention. The dipstick comprises a porous material capable of chromatographically, transporting a liquid and one or more of the antibodies mentioned herein. When the dipstick is contacted with the sample it draws up liquid from the sample towards a detection region on the dipstick. Peptides in the sample which derive from proANP or proBNP are detected by their binding to the detection region.

In one embodiment the liquid is drawn through a region in the dipstick containing the antibodies of the invention. These antibodies bind to the relevant peptides forming an antibody/peptide complex. This complex is drawn towards the detection region which contains an agent (immobilised on the dipstick) that binds and thus immobilises the complex in the detection region. This agent is typically a specific binding agent (e.g an antibody) that binds either the antibody or the peptide of the complex. The antibody/peptide complex is typically detected in the detection region by the use of a label which is attached to the specific antibody.

In another embodiment protein in the sample is labelled before it is drawn up the dipstick. The labelled protein is then drawn up the dipstick (which has been contacted with sample) and is detected by binding the polymorphism specific antibody (which is bound to the detection region).

Typically the label used in the dipstick systems described above is a visually detectable label which becomes visually detectable (i.e. can be seen with the human eye) when enough antibody/protein complex becomes immobilised in the detection region. A suitable label is a gold (or other colloidal metal) particle or a fluorophore (e.g. fluoroscein).

The dipstick may comprise a denaturing agent that causes denaturation of the protein which is drawn up the dipstick. In one embodiment the sample is exposed to denaturing conditions (e.g. contacted with a denaturing agent) before it is contacted with the dipstick.

Agents of the Invention (proXNP, NT-proXNP, XNP)

(a) Peptide Agents

In one embodiment the present test method utilises an agent (proXNP, XNP or NT-proXNP) which comprises amino acid sequence derived or originating from both proANP and proBNP. The agent mimics proANP- and proBNP-derived peptides in the sample to be tested in particular, naturally occurring peptides. The agent for use in the present method is also recognised or bound by the first binding substance to be used in the method. Thus the agent can compete with the peptides in a sample for binding to the first binding substance in the assays of the invention. An agent may also be used as a calibrator or standard in an assay. Thus the agents are particularly useful for quantifying peptides derived from proANP and proBNP in a sample. For example, in the present assay methods, the measure of peptides in a sample may be expressed as a concentration of agent. Furthermore the agent may be used as an immunogen to produce antibody suitable for use as a first binding substance, according to the methods set out above.

The agent may comprise or consist essentially of a peptide, polypeptide or protein. For example, an agent may comprise or consist of a fusion protein. An agent according to the invention generally comprises sequence characteristic of proANP and sequence characteristic of proBNP. Thus an agent typically includes at least one peptide sequence derived from proANP and at least one peptide sequence derived from proBNP.

In particular an agent may comprise both:
(a) (i) SEQ ID Nos 1, 2 or 3;
   (ii) an homologous variant of (i); or
   (iii) a fragment of (i) or (ii);
and
(b) (i) SEQ ID Nos 4, 5 or 6;
   (ii) an homologous variant of (i); or
   (iii) a fragment of (i) or (ii).

In one embodiment the agent comprises both:
(a) (i) SEQ ID Nos 1, 2 or 3;
   (ii) a homologous sequence having at least 70% identity to (i); or
   (iii) a fragment of (i) or (ii) which is at least 6 amino acids in length;
and
(b) (i) SEQ ID Nos 4, 5 or 6;
   (ii) a homologous sequence having at least 70% identity to (i); or
   (iii) a fragment of (i) or (ii) which is at least 6 amino acids in length.

In one aspect an agent comprises amino acids 7 to 23 of ANP and/or amino acids 10 to 26 of BNP, or variants thereof. These peptides form a conserved ring structure in nature ANP and BNP, which may be conserved in the agent. In one embodiment, an agent comprises an epitope of proANP and/or proBNP. For example, suitable epitopes include amino acids 5 to 13, 1 to 10, 15 to 25 or 27 to 32 of BNP and amino acids 65 to 76 or 1 to 13 of NT-proBNP. In one embodiment an agent includes peptide sequence derived (according to the above) from both NT-proANP and NT-proBNP (such an agent is referred to as NT-proXNP), or from both ANP and BNP (the agent being then referred to as XNP).

In one embodiment the agent may comprise peptide sequence selected from one or more of proBNP$_{1-37}$, proBNP$_{15-24}$, proBNP$_{10-29}$, proBNP$_{77-92}$, proBNP$_{1-108}$, proANP$_{29-98}$, proANP$_{82-96}$, proANP$_{20-80}$, proANP$_{60-80}$, proANP$_{112-126}$ or variants thereof. In one aspect an agent comprises at least one proBNP and at least one proANP sequence selected from this list. Suitable combinations are proBNP$_{15-24}$ and proANP$_{82-96}$, proBNP$_{1-37}$ and proANP$_{29-98}$, proBNP$_{10-29}$ and proANP$_{20-80}$, proBNP$_{10-29}$ and proANP$_{60-80}$, proBNP$_{1-108}$ and proANP$_{1-126}$ or proBNP$_{77-92}$ and proANP$_{112-126}$. Thus an agent according to the invention may comprise or consist of NT-proXNP1 (SEQ ID NO:13), NT-proXNP2 (SEQ ID NO:14), NT-proXNP3 (SEQ ID NO:15), NT-proXNP4 (SEQ ID NO:17), NT-proXNP5 (SEQ ID NO: 18), proXNP6 (SEQ ID NO: 19) or XNP7 (SEQ ID NO: 20).

In addition to the peptide sequences derived from proANP and proBNP the agent may include linker, connector or adduct amino acid sequence of variable length or composition. Suitable linkers are known in the art. The structure of the linker may be such as to allow attachment of one or more labels (eg fluorescent groups or enzymes) to the linker. For example, suitable spacers and adducts include Gly-Lys-Tyr-Gly (GKYG) (SEQ ID NO: 16), Ser-Arg, Gly-Ser or a single amino acid such as Tyr or Cys. The Tyr residue permits radioiodination and the Lys or Cys residue allows attachment of labels requiring an amino group or sulphydryl group.

An agent may be immobilised on a solid support, such as those described for antibodies.

An agent of the invention may comprise chemically modified amino acid sequence, e.g. post-translationally modified. For example, it may be glycosylated or comprise modified amino acid residues. It may be modified by the addition of histidine residues to assist purification. It may be desirable to produce peptide or protein in a form suitable for attachment to a solid support. Protein or peptide may thus be modified to enhance its binding to a solid support for example by the addition of a cysteine residue.

(b) Polynucleotides Encoding Agents

The invention also relates to polynucleotides which encode an agent according to the invention or the peptide part of an agent according to the invention. Such polynucleotides comprise sequence which encodes the agent peptides as defined above and/or sequence which is complementary to the coding sequence.

In particular a polynucleotide of the invention may comprise both:
(a) (i) SEQ ID NOs 7, 8 or 9;
   (ii) a sequence complementary to (i);
   (iii) a sequence which hybridises under stringent conditions to (i) or (ii);
   (iv) a sequence which is degenerate as a result of the genetic code to (i), (ii) or (iii);
   (v) a sequence having at least 70% identity to any of the sequences in (i) to (iv); or
   (vi) a fragment of any of the sequences in (i) to (v);
and
(b) (i) SEQ ID NOs 10, 11 or 12;
   (ii) a sequence complementary to (i);
   (iii) a sequence which hybridises under stringent conditions to (i) or (ii);
   (iv) a sequence which is degenerate as a result of the genetic code to (i), (ii) or (iii);
   (v) a sequence having at least 70% identity to any of the sequences in (i) to (iv); or
   (vi) a fragment of any of the sequences in (i) to (v).

A polynucleotide may also comprise nucleotide sequence encoding linker or spacer amino acid sequence in the agent. A polynucleotide of the invention typically comprises 1000 base pairs or less, for example 500 base pairs or less. A polynucleotide may comprise up to 200, 300, 400, 500, 600, 700, 800 or 900 base pairs. For example, a polynucleotide may comprise up to 50, 100, 150 or 175 nucleotides.

Typically the polynucleotide is DNA. However, the invention may comprise RNA polynucleotides. The polynucleotides may be single or double stranded, and may include within them synthetic or modified nucleotides.

A polynucleotide of the invention can hybridize to the coding sequence or the complement of the coding sequence of the specified sequence (any of SEQ ID NOs: 7-12) at a level significantly above background. Background hybridization may occur, for example, because of other DNAs present in a DNA library. The signal level generated by the interaction between a polynucleotide of the invention and the coding sequence or complement of the coding sequence of the specific sequence is typically at least 10 fold, preferably at least 100 fold, as intense as interactions between other polynucleotides and the coding sequence of the specific sequence. The intensity of interaction may be measured, for example, by radiolabelling the probe, e.g. with $^{32}$P. Selective hybridisation may typically be achieved using conditions of medium to high stringency. However, such hybridisation may be carried out under any suitable conditions known in the art (see Sambrook et al, 1989) For example, if high stringency is required suitable conditions include from 0.1 to 0.2×SSC at 60° C. up to 65° C. If lower stringency is required suitable conditions include 2×SSC at 60° C.

The coding sequence of any of SEQ ID NOs: 7-12 may be modified by nucleotide substitutions, for example from 1, 2 or 3 to 10, 25 or 50 substitutions. The polynucleotide of any of SEQ ID NOs: 7-12 may alternatively or additionally be modified by one or more insertions and/or deletions and/or by an extension at either or both ends. Additional sequences such as signal sequences may also be included. Degenerate substitutions may be made and/or substitutions may be made which would result in a conservative amino acid substitution when the modified sequence is translated, for example as shown in the Table included in the Variants section above.

A nucleotide sequence which is capable of selectively hybridizing to the complement of the DNA coding sequence of any of SEQ ID NOs: 7-12 will generally have at least 70%, at least 80%, at least 90%, at least 95%, at least 98% or at least 99% sequence identity to the specific coding sequence over a region of at least 20, for example at least 30, for instance at least 40, at least 60, 80, 100 for instance 100 or 200 or more nucleotides or most preferably over the full length of the specific coding sequence For example the UWGCG Package provides the BESTFIT program which can be used to calculate homology (for example used on its default settings) (Devereux et al (1984) *Nucleic Acids Research* 12, p 387-395). The PILEUP and BLAST algorithms can be used to calculate homology or line up sequences (typically on their default settings), for example as described in Altschul (1993) J. Mol. Evol. 36:290-300; Altschul et al (1990) J. Mol. Biol. 215:403-10.

Software for performing BLAST analyses is publicly available through the National Centre for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, 1990). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Natl. Acad. Sci. USA* 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) *Proc. Natl. Acad. Sci. USA* 90: 5873-5877. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

Any combination of the above mentioned degrees of sequence identity and minimum sizes may be used to define polynucleotides of the invention, with the more stringent combinations (i.e. higher sequence identity over longer lengths) being preferred. Thus, for example a polynucleotide which has at least 90% sequence identity over 25, preferably over 30 nucleotides forms one aspect of the invention, as does a polynucleotide which has at least 95% sequence identity over 40 nucleotides.

Fragments of polynucleotides may be for example, up to 40, or up to 30 nucleotides in length. Preferably the length is up to 5, 10, 15, 20 or 25 nucleotides.

In one embodiment, a polynucleotide encoding an agent of the invention may comprise any of SEQ ID NOS: 21 to 27. Thus a polynucleotide may encode NT-proXNP1, NT-proXNP2, NT-proXNP3, NT-proXNP4, NT-proXNP5, proXNP6 or XNP7.

A polynucleotide may comprise:
(a) SEQ ID NO 21, 22, 23, 24, 25, 26 or 27;
(b) a sequence complementary to (a);
(c) a sequence which hybridises under stringent conditions to (a) or (b);
(d) a sequence which is degenerate as a result of the genetic code to (a), (b) or (c);
(e) a sequence having at least 70% identity to any of the sequences in (a) to (d); or
(f) a fragment of any of the sequences in (a) to (e).

Polynucleotides according to the invention may, be produced recombinantly, synthetically, or by any means available to those of skill in the art. They may also be cloned by standard techniques. The polynucleotides are typically provided in isolated and/or purified form.

In general, primers will be produced by synthetic means, involving a step wise manufacture of the desired nucleic acid sequence one nucleotide at a time. Techniques for accomplishing this using automated techniques are readily available in the art, Although in general the techniques mentioned herein are well known in the art, reference may be made in particular to Sambrook et al, Molecular Cloning: A Laboratory Manual, 1989.

The polynucleotides according to the invention have utility in production of the polypeptide agents according to the invention, which may take place in vitro, in vivo or ex viva. The polynucleotides may be used in recombinant protein synthesis. Recombinant protein expression methods are known in the art and are discussed further below.

Polynucleotides or primers of the invention may carry a revealing label. Suitable labels include radioisotopes such as $^{125}$I, $^{32}$P or $^{35}$S, enzyme labels, or other protein labels such as biotin. Such labels may be added to polynucleotides or primers of the invention and may be detected using techniques known per se.

(c) Vectors, Host Cells and Expression of Peptide Agents

The polynucleotides of the invention may be incorporated into a recombinant replicable vector. The vector may be used to replicate the nucleic acid in a compatible host cell. Therefore, polynucleotides of the invention may be made by introducing a polynucleotide of the invention into a replicable vector, introducing the vector into a compatible host cell and growing the host cell under conditions which bring about replication of the vector.

In one aspect the vector is an expression vector comprising a nucleic acid sequence that encodes a polypeptide agent of the invention. Such expression vectors are routinely constructed in the art of molecular biology and may, for example, involve the use of plasmid DNA and appropriate initiators, promoters, enhancers and other elements, which may be necessary, and which are positioned in the correct orientation, in order to allow for protein expression. Other suitable vectors would be apparent to persons skilled in the art. By way of further example in this regard we refer to Sambrook et al. 1989.

In one embodiment, a polynucleotide of the invention or for use in the invention in a vector is operably linked to a control sequence which is capable of providing for the expression of the coding sequence by the host cell, i.e. the vector is an expression vector. The term "operably linked" refers to a juxtaposition wherein the components described are in a relationship permitting them to function in their intended manner. A regulatory sequence, such as a promoter, "operably linked" to a coding sequence is positioned in such a way that expression of the coding sequence is achieved under conditions compatible with the regulatory sequence.

The vectors may be for example, plasmid, virus or phage vectors provided with a origin of replication, optionally a promoter for the expression of the said polynucleotide and optionally a regulator of the promoter. The vectors may contain one or more selectable marker genes, for example an ampicillin resistance gene in the case of a bacterial plasmid or a resistance gene for a fungal vector.

Promoters and other expression regulation signals may be selected to be compatible with the host cell for which expression is designed. For example, yeast promoters include *S. cerevisiae* GAL4 and ADH promoters, *S. pombe* nmt1 and adh promoter. Mammalian promoters include the metallothionein promoter which can be induced in response to heavy metals such as cadmium. Viral promoters such as the SV40 large T antigen promoter or adenovirus promoters may also be used. All these promoters are readily available in the art.

Mammalian promoters, such as β-actin promoters, may be used. Tissue-specific promoters may be used. Viral promoters may also be used, for example the Moloney murine leukaemia virus long terminal repeat (MMLV LTR), the rous sarcoma virus (RSV) LTR promoter, the SV40 promoter, the human cytomegalovirus (CMV) IE promoter, adenovirus, HSV promoters (such as the HSV IE promoters), or HPV promoters, particularly the HPV upstream regulatory region (URR). Viral promoters are readily available in the art.

Vectors may be used in vitro, for example for the production of DNA or RNA or used to transfect or transform a host cell, for example, a mammalian host cell.

Expression vectors may be transformed into a suitable host cell to provide for expression of a polypeptide agent of the invention or a peptide component of agent according to the invention. The host cell, transformed or transfected with an expression vector as described above, is cultivated under conditions to allow for expression of the polypeptide or fragment, and the expression product is recovered. The polypeptide may be isolated and purified using methods known in the art. For example, phage display techniques may be used. Host cells will be chosen to be compatible with the vector and will preferably be bacterial. Host cells may also be cells of a non-human animal, or a plant transformed with a polynucleotide of the invention.

General

Any of the agents, polypeptides, polynucleotides, vectors, cells or antibodies of the invention may be present in substantially isolated form. They may be mixed with carriers or diluents which will not interfere with their intended use and still be regarded as substantially isolated. They may also be in substantially purified form, in which case they will generally comprise at least 90%, e.g. at least 95%, 98% or 99% of the proteins, polynucleotides, cells or dry mass of the preparation.

Any of the agents, or antibodies of the invention may be labelled, generally with a suitable detectable label. For example, suitable labels include radiolabels, enzyme labels (e.g. alkaline phosphatase and peroxidase e.g. HRP), chemical labels such as biotin (which may be detected by avidin or streptavidin conjugated to peroxidase), lanthanides such as europium and fluorescent labels (e.g. fluorescein and rhodamine), and luminescent or chemiluminescent labels (e.g. acridinium ester, luminol), gold (or other colloid metal) a dye or a particle. Enzyme labels may be detected using a chemiluminescence or chromogenic based system.

Diagnostics and Monitoring Treatment

The present methods are useful for assessing cardiac health in an individual. In particular, the methods may be used to detect and assess cardiac impairment. A particular example of cardiac disease that may be targeted using the present methods is congestive heart failure.

Heart failure is a clinical condition characterised by the inability of the heart to generate a cardiac output sufficient to meet the demands of the body resulting in an activation of the ANP and BNP hormonal systems. Activation of the ANP system is initially associated mainly with atrial overload whereas activation of the BNP system is primarily suggestive of ventricular overload. Inactivation of the systems is a result of either the patient's own regulatory systems or the use of therapeutic drugs for treatment of heart failure.

As above, the present methods, by determining the combined levels of peptides derived from proANP and proBNP in a sample relative to a reference peptide level, can be used to determine activation or inactivation of both the ANP and BNP hormonal systems in an individual. Thus, the present methods may be used to assess functioning of the cardiac systems. The methods of the invention are useful for screening and ruling out of, assessment of severity of, assessment of prognosis, follow up of treatment and guidance of treatment of cardiac disease such as heart failure in patients with cardiac pressure or volume overload.

For example, the methods may be used for diagnosis of cardiac disease. The methods may be used to screen individuals, to assess the severity of cardiac condition, to assess prognosis or to gauge susceptibility to, for example cardiac failure. The present methods may also be employed as a follow-up to treatment for cardiac disease and to assess, monitor and guide treatment of cardiac disease. By monitoring activation or inactivation of the ANP and BNP systems according to the present methods, it is possible to assess the effects of treatment in patients suffering heart disease, for example pharmacological therapy. Thus the present methods may be used to assess patient responsiveness to a particular therapy and to improve the treatment which is provided.

The present methods may be used to assess susceptibility to cardiac disease. Individuals may then be advised on lifestyle changes which may be required to decrease the likelihood of developing or decrease the severity of symptoms associated with cardiac disease such as heart failure. Individuals may be treated prophylactically for the same purpose.

Diagnostic Kits

The invention also provides a diagnostic kit. The kit is suitable for use in the present methods and is in general useful for diagnosis and assessment of cardiac condition as described above.

The contents of the kit will be suitable for the assay format that the kit is intended for. Typically the kit comprises a first binding substance as defined herein, and optionally means for detecting binding complexes formed by the first binding substance, also as described herein. A kit may additionally comprise an agent according to the invention, the agent being able to bind to the first binding substance in the kit. The first binding substance and/or the agent may be labelled.

In general a kit may comprise other reagents or components for use in the particular assay, such as buffers, precipitators, labelling and/or detection means. In one embodiment the kit will include instruction means, such as a package insert instructing the user of the kit as to the kit contents and assay format.

Thus, a kit for a competitive assay may comprise:
  (a) a first binding substance;
  (b) labelled agent (NT-proXNP, proXNP or XNP);
  (c) a standard (NT-proXNP, proXNP or XNP); and
  (d) other usual materials according to the detection system, eg. precipitators, buffers etc.

A kit for a sandwich assay may comprise:
  (a) first binding substance;
  (b) labelled second binding substance;
  (c) a standard (NT-proXNP, proXNP, XNP);
  (c) other usual materials according to the detection system.

EXAMPLES

The following Examples illustrate the invention. Unless indicated otherwise, the methods used are standard biochemistry and molecular biology techniques. Examples of suitable general methodology textbooks include Sambrook et al, Molecular Cloning, A Laboratory Manual (1989) and Ausubel et al, Current Protocols in Molecular Biology (1995) John Wiley and Sons Inc.

Example 1

Expression and Purification of Recombinant NT-proXNP

The nucleotides encoding amino acids 1-37 of human NT-proBNP and those encoding amino acids 29-98 of human NT-proANP are amplified by reverse transcription PCR from human atrial RNA using oligonucleotide primers. The 5'-primer for NT-proBNP amplification contains the cleavage site for the restriction enzyme BamHI (5'-GCGGATCCCAC-CCGCTGGGCAGCCCCG-3' Seq ID NO:28) and the 3'-primer for XbaI (5'-GCTCTAGAGGATGTCTGCTC-CACC-3' SEQ ID NO:29). The 5'-primer for NT-proANP amplification has XbaI linker (5'-GCTCTAGAGAAGAT-GAGGTCGTGC-3' SEQ ID NO:30) and the 3'-primer has EcoRI linker (5'-GCGAATTCTCACCGAGGGGCAGT-GAGC-3' SEQ ID NO:31). In addition, the NT-proANP amplicon contains an in-frame termination codon (TGA) at its 3'-end preceding the EcoRI cleavage site. The other version of NT-proBNP amplicon contains an in-frame codon for Tyr at its 5'-terminus following the BamHI linker sequence (5'-GCGGATCCTACCACCCGCTGGGCAG-3' SEQ ID NO:32). The RT-PCR products, are purified by agarose electrophoresis, cleaved with XbaI and BamHI or EcoRI and subcloned end-to-end (NT-proBNP->NT-proANP) into BamHI/EcoRI site of pGEX-4T-1 vector (Amersham Pharmacia Biotech, Uppsala, Sweden). The nucleotide sequences and reading frames of the constructs are confirmed by sequencing.

The expression and affinity purification of the GST-proteins are carried out according to the following procedure. An overnight culture of *E. coli*, transformed with a recombinant plasmid, is diluted 1:100 in 2×YTA and grown at 37° C. until the OD at 660 nm reaches 0.6. Isopropyl-1-thio-D-galactopyranoside (IPTG) is added to a final concentration of 0.1 mM and the culture is further incubated for 1-2 h. The bacterial cells are harvested by centrifugation (7000 g for 10 min. at +4° C.), resuspended in PBS (50 µl/ml of culture) and sonicated. The cell lysate is cleared at 7000 g for 15 min. The supernatant is applied to a glutathione agarose column (Sigma, Saint Louis, Mo., USA) and washed three times with PBS. The fusion protein is eluted with 10 mM glutathione in 50 nM Tris-HCl, pH 8.0 and stored in aliquots at 20° C. Samples are separated by SDS-PAGE (12% acrylamide). Both prokaryotic or eukaryotic expression vectors can be used. Accordingly, the whole peptide or at least a portion of said peptide or protein may be produced in prokaryotic or eukaryotic cells.

The recombinant peptides are released from fusion partner by treating with thrombin (Amersham Pharmacia Biotech) at room temperature for 1 h (1 U/100 µg protein). The peptides are purified by reverse-phase HPLC using a 4.6×150 mm Vydac $C_4$ column. The column is eluted with a linear 40 min gradient from 20-48% acetonitrile in aqueous trifluoroacetic acid. Elution rate is 1 ml/min and absorbance at 200-280 nm is measured during HPLC to monitor the purity of products.

An example of the HPLC profile of the purified product consisting of (from $NH_2$ to $CO_2H$-terminus) human proBNP$_{1-37}$, a short spacer, serine and arginine, and human proANP$_{29-98}$, is presented in FIG. 1. Two additional amino acids, glycine and serine, originated from GST are left in the N-terminus of the peptide as an adduct.

Example 2

Chemical Synthesis of NT-proXNP

The combination epitope NT-proXNP5 comprising (from $NH_2$— to $CO_2H$ terminus) the sequences human proBNP$_{10-29}$, Cys spacer and human proANP$_{60-80}$ was assembled with a Peptide Synthesizer using Fmoc chemistry. Alternatively the combination epitope peptide NT-proXNP1 comprising (from $NH_2$- to $CO_2H$-terminus) the sequences human proBNP$_{15-24}$, Gly-Lys-Tyr-Gly spacer and human proANP$_{82-96}$, was assembled. The product was cleaved from the HMP resin with 95% trifluoroacetic acid/2.5% $H_2O$, 2.5% tri-isopropylsilane, precipitated with diethyl ether, dried and desalted on Sephadex G-15 in 30% acetic acid. The peptide was purified by reverse phase HPLC in a preparative RCM NovaPak $C_{18}$ cartridge (2.5×10 cm) with a linear gradient of acetonitrile in aqueous 0.1% trifluoroacetic acid. The purity was ascertained by reverse phase HPLC in elution conditions with different selectivity. The identity of the peptide was confirmed by amino acid analysis or MALDI-TOF mass spectrometry and peptide mapping.

Example 3

Immunoassay of NT-proXNP

Binding substance was prepared from goat antibodies obtained by using as immunogen affinity purified, fusion protein of GST/NT-proANP$_{20-80}$ and NT-proBNP$_{10-29}$-TBG or GST-fusion protein of NT-pro-BNP$_{1-37}$ and NT-proANP$_{29-98}$. The latter of the peptide antigens was prepared with the methods described in Example 1 and contains human proBNP$_{1-37}$, Ser-Arg spacer, human proANP$_{29-98}$ and Gly-Ser adduct. Alternatively, another peptide antigen was prepared with the methods described in Example 2 comprising (from NH$_2$— to CO$_2$H terminus) the sequences human proBNP$_{10-29}$, cysteine spacer from which it was coupled to bovine thyroglobulin (TBG) prior to immunisation and human proANP$_{60-80}$. Goats were injected at multiple sites at the back with 1-1.5 mg of immunogen in 1 ml 0.9% NaCl emulsified in equal volume of Freund's complete adjuvant. Boosters of 0.5 mg in Freund's incomplete adjuvant were given 2-4 times at 2-3 weeks intervals and blood is drawn 14 days after the fast injections. The antisera were chosen according to the titre of binding the radioiodinated peptide or protein agent of the invention (see below), as well as the sensitivity and specificity with regard to related peptides and peptide or protein agent of the invention. Any modification of the peptide or protein agent of the invention or any fragment or derivative thereof may also be used for immunisation purposes to produce either monoclonal or polyclonal antibodies.

Recombinant NT-proBNP$_{1-37}$/NT-proANP$_{29-98}$ (1.5 µg), produced as described in Example 1, was radioiodinated using 0.5 mCi Na$^{125}$I in the presence of 10 µg chloramine-T in 0.5 M phosphate buffer, pH 7.5 for 60 sec., followed by the addition of 10 µg sodium disulphite. The mixture was desalted by Sephadex G-25 gel filtration and purified by reverse phase HPLC in a Symmetry C$_{18}$ column and a 30 min linear 20% to 50% acetonitrile gradient in aqueous trifluoroacetic acid at a flow rate of 1 ml/min. Fractions of 1 ml were collected and monitored for radioactivity in a Multi-Gamma counter (Wallac, Turku, Finland).

Recombinant NT-proBNP$_{1-37}$/NT-proANP$_{29-98}$, produced as described in Example 1, was used also as the assay calibrator in the NT-proXNP immunoassay. The assay buffer used for all dilutions consists of 0.04 M sodium hydrogen phosphate, 0.01 M sodium dihydrogen phosphate, 0.1 M NaCl, 0.1% gelatine, 0.05% Triton X-100, pH 7.4). Plasma or serum samples were incubated in duplicates of 25 µl with 100 µl of antiserum and 100 µl of tracer solution (containing approx. 8 000 cpm of iodinated peptide) for 16-24 h at +4° C. Calibration was performed by incubating calibrators (0.08-8 nmol l$^{-1}$) with the same amount and concentration of antiserum, tracer and anti-antiserum for the same time period as above. The amount of antiserum assayed was determined to bind 40-50% of the tracer when no competitor was present, in order to ensure sufficient competition in binding.

Figure 2A:
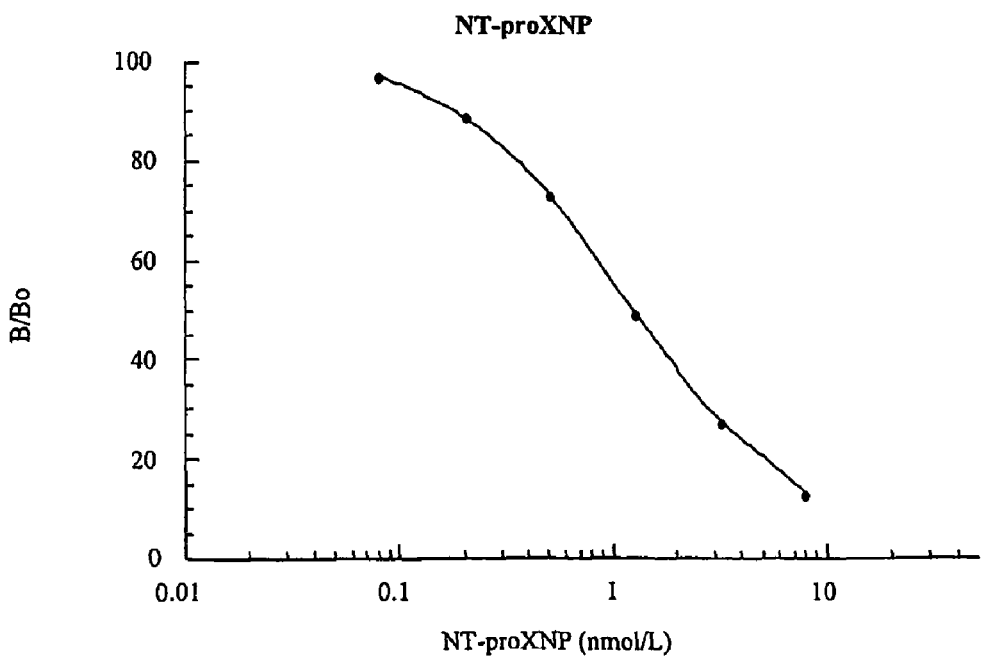
FIG. 2a: A competitive binding curve for immunoassay of NT-proXNP.
Figure 2B:
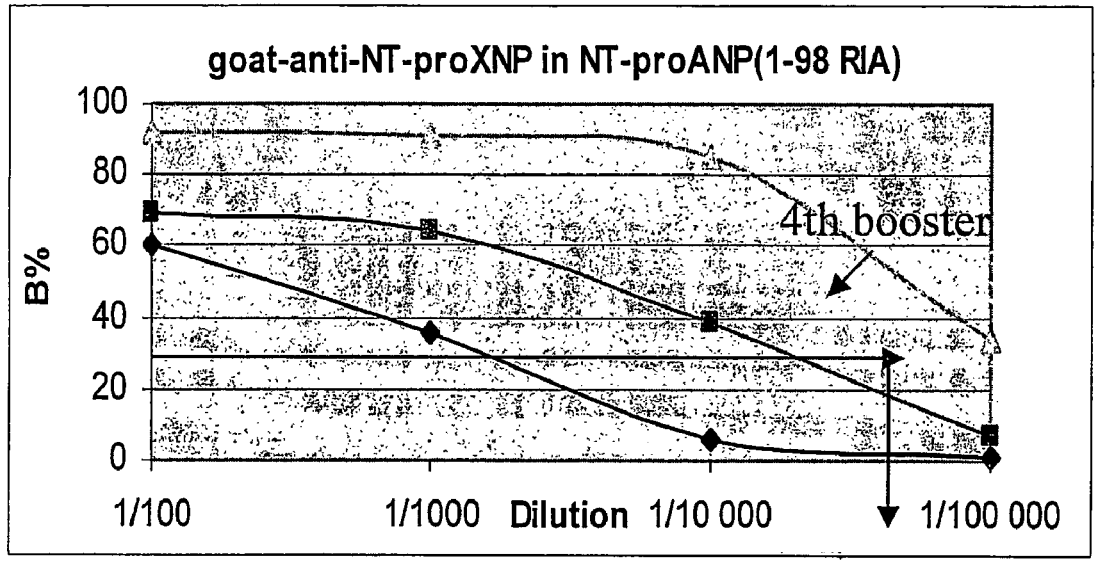
FIG. 2b: Development of antibody titres in immunisation of a goat using a GST-fusion protein of NT-proXNP2 as immunogen.
Figure 2B:
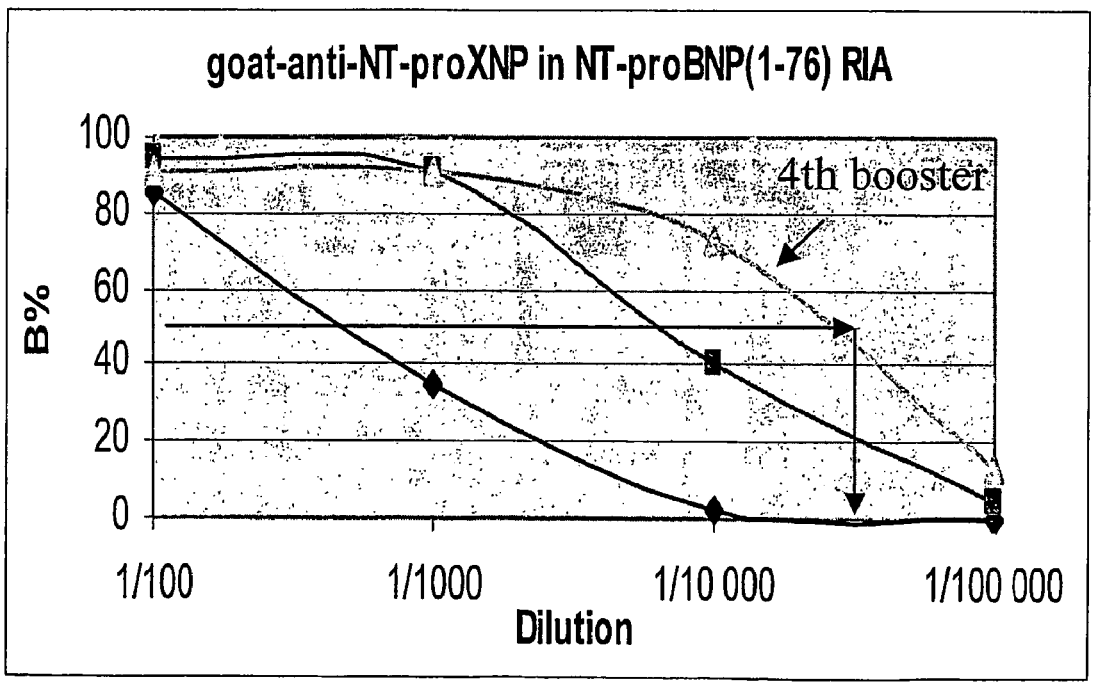

FIG. 2b shows development of antibody titres in immunisation of a goat using GST-fusion protein of NT-proBNP$_{1-37}$/NT-proANP$_{29-98}$ (comprising SEQ ID NO: 14) as immunogen, titres after 1$^{st}$, 3$^{rd}$ and 4$^{th}$ booster in RIA of NT-proANP$_{1-98}$ and NT-proBNP$_{1-76}$. FIG. 2b shows that, for example, a binding substance prepared in a goat, obtained by using GST-fusion protein of NT-proBNP$_{1-37}$/NT-proANP$_{29-98}$ (comprising SEQ ID NO: 14) as immunogen, typically in dilution of 1:50,000-1:60,000 was suitable for 40-50% binding and simultaneous binding of NT-proANP (SEQ ID NO: 3) and NT-proBNP (SEQ ID NO: 6) demonstrated also in separate radioimmunoassay of NT-proANP$_{1-98}$ and NT-proBNP$_{1-76}$. A similar binding substance was produced in immunisation of a goat using TBG-conjugate of NT-proBNP$_{10-29}$/NT-proANP$_{60-80}$, (comprising SEQ ID NO: 18) as immunogen. A typical dilution in competitive NT-proXNP assay was ranging from 1:10,000 to 1:15,000.

Bound and free NT-proXNP were separated by precipitation with donkey anti-goat IgG in 0.5 ml of 8% polyethylene glycol 6000, containing normal goat serum carrier (1 µl). After centrifugation, the pellet was counted for radioactivity. An example of a reference curve obtained by this type of assay is presented in FIG. 2a.

FIG. 2a shows a competitive binding curve for immunoassay of NT-proXNP. The assay utilises recombinant NT-proBNP$_{1-37}$/NT-proANP$_{29-98}$ as calibrator and tracer and polyclonal goat antibody based binding substance to recognise NT-proXNP, NT-proANP and NT-proBNP simultaneously. The X-axis depicts the amount of calibrator added and the Y-axis Bound/Bound with no calibrator added.

Figure 3:
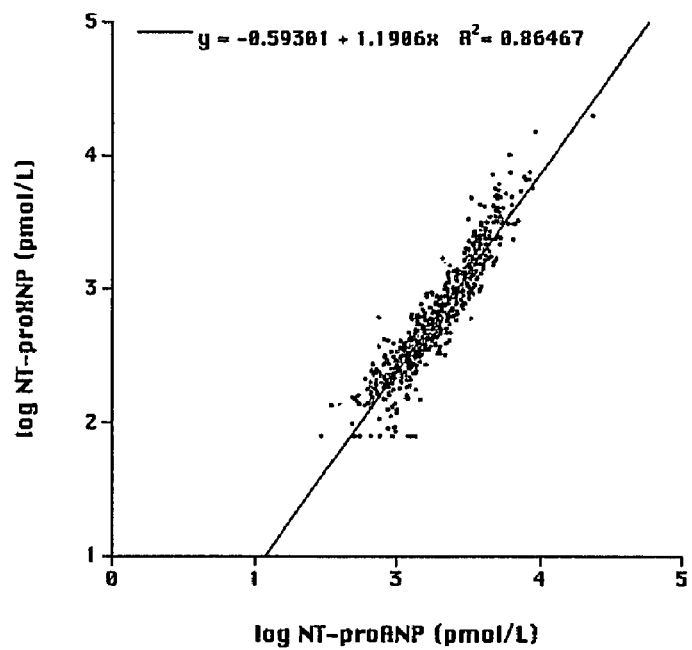
FIG. 3: Serum levels of NT-proANP, NT-proBNP and NT-proXNP in patients with cardiac disorders.
Figure 3:
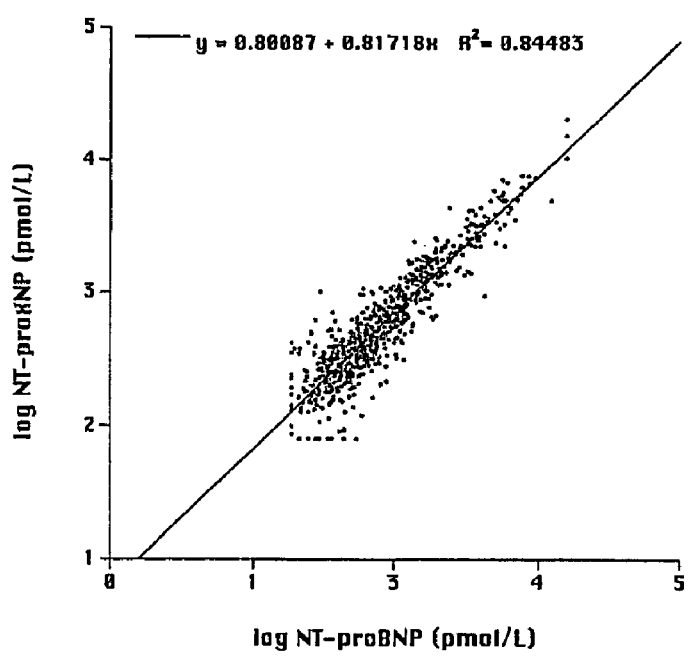

The immunoassay of NT-proXNP described in Example 3 was used to determine the serum levels of NT-proXNP in 700 patients with cardiac disorders. The results are shown in FIG. 3. The levels of NT-proXNP are highly significantly correlating with NT-proANP and NT-proBNP levels measured from the same samples by separate in-house radioimmunoassays of NT-proANP$_{1-98}$ and NT-proBNP$_{1-76}$.

Figure 4:
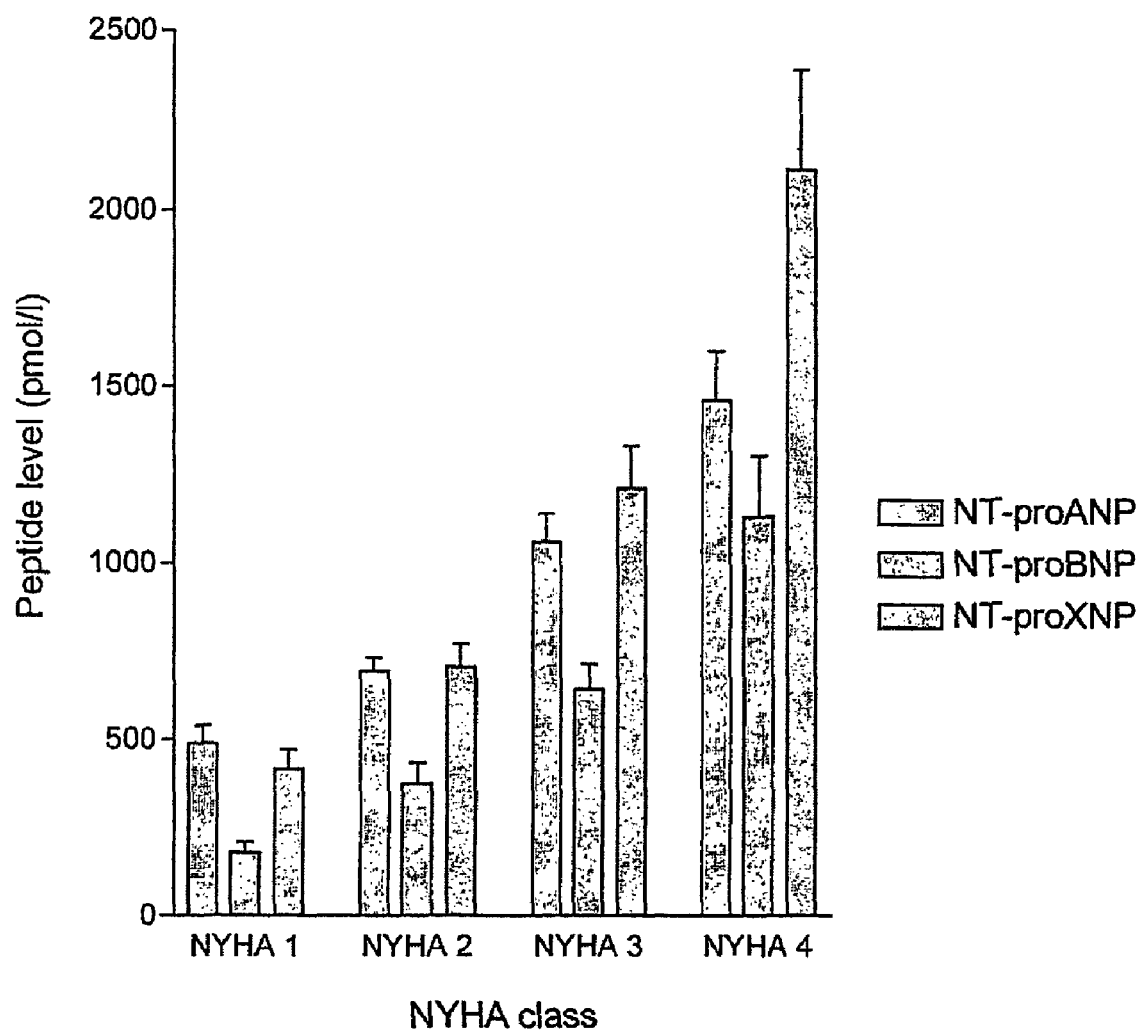
FIG. 4: Serum levels of NT-proANP, NT-proBNP and NT-proXNP in cardiac patients.

The methods of Example 3 were used to assay the serum levels of NT-proXNP, in 500 cardiac patients classified according to the New York Heart Association (NYHA) scale. The results are shown in FIG. 4. The serum levels of NT-proANP and NT-proBNP measured by separate in-house radioimmunoassays from the same samples are displayed for reference as measure of activation ANP and BNP systems.

Figure 5:
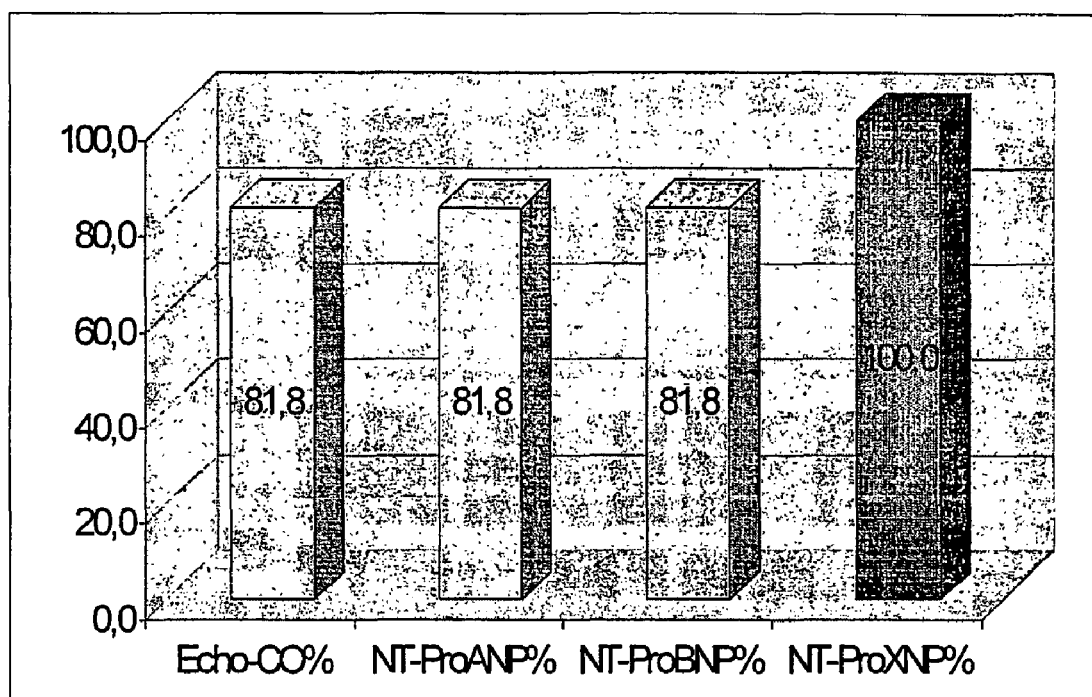
FIG. 5: Response of plasma NT-proANP, NT-proBNP and NT-proXNP and cardiac output (CO) in patients of heart failure to therapy.

The methods of Example 3 were used to assay plasma levels of NT-proXNP in patients suffering heart failure and these were correlated with positive effect of pharmacological therapy in the patients. Results are shown in FIG. 5. The serum levels of NT-proANP and NT-proBNP measured from the same samples by separate in-house radioimmunoassays are displayed for reference. Patients (n=11) suffering from heart failure (stabile NYHA class II-III) were treated by intravenous infusion of an inodilatator for 24 hours. Cardiac output (CO) as ml/min was measured with echocardiography. The levels of NT-proANP, NT-proBNP and NT-proXNP were assayed before and at time point of 24 hours from the start of administration of the drug. The relative sensitivity to detect response to the treatment was determined at the cut-off levels of 10% increase in CO, as determined with echocardiography and 20% decrease in NT-ProANP and NT-ProBNP and NT-proXNP as measure of inactivation of ANP and BNP systems. NT-proXNP exceeded cut-off in all of 11 cases, whereas NT-proANP and NT-proBNP and CO excluded cut off in 9 of 11 cases.

REFERENCES

Altschul et al., J. Mol. Biol. (1990) 215: 403-410
Altschul et al., J. Mol. Evol. (1993) 36: 290-300
Ausubel et al., Current Protocols in Molecular Biology (1995) John Wiley & Sons Inc
Daly C et al.: Natriuretic peptides in the diagnosis of heart disease—First amongst equals? In J Cardiol 2002; 84:107-13.
De Lemos J A et al.: The prognostic value of B-type natriuretic peptide in patients with acute coronary syndromes. N Engl J Med 2001; 345:1014-21.
Devereux et al., Nucleic Acids Research (1984) 12: 387-395
Drewett J G, Garbers D L: The family of guanylyl cyclase receptors and their ligands. Endocrine Rev 1994; 15:135-62.
Dzimiri N, Moorji A, Afrane B, Al-Halees Z. Differential regulation of atrial and brain natriuretic peptides and its implications for the management of left ventricular volume overload. Eur J Clin Invest 2002; 32:563-9.

Harlow and Lane "Antibodies: A Laboratory Manual", Cold Spring Harbor Laboratory Press, Cold Spring Harbor, N.Y. (1988)

Henikoff and Henikoff, Proc. Natl. Acad. Sci. USA (1992) 89: 10915-10919

Kannel W B et al.: Changing epidemiological features of heart failure. Br Heart J 1994; 72:S3-S9

Karlin and Altschul, Proc. Natl. Acad. Sci. USA (1993) 90: 5873-5877

Köhler G, Milstein C: Continuous cultures of fused cells secreting antibody of predefined specificity. Nature 1975; 256:495-7.

McDonagh T A et al.: Symptomatic and asymptomatic left-ventricular systolic dysfunction in an urban population. Lancet 1997; 350:829-33.

Maddox et al., J. Exp. Med. (1993) 158: 1211-1226

Misono K, Sivasubramanian N, Berkner K, Xhang X. Expression and purification of the extracellular ligand-binding domain of the atrial natriuretic peptide (ANP) receptor: monovalent binding with ANP induces 2:2 complexes. Biochemistry 1999; 38:516-23

Omland T et al.: N-terminal pro-B-type natriuretic peptide and long-term mortality in acute in coronary syndromes. Circulation 2002; 106:2913-8.

Remes M, Miettinen H, Reunanen A, Pyörälä K. Validity of clinical diagnosis of heat failure in primary health care. Eur Heart J 1991; 12:315-21.

Sagnella G A: Measurement and significance of circulating natriuretic peptides in cardiovascular diseases. Clin Sci 1998; 95:519-29.

Sambrook et al. Molecular Cloning, A Laboratory Manual (1989)

Skerra A, Plückthun A: Assembly of a functional immunoglobulin Fv fragment in *Escherichia coli*. Science 1988; 240:1038-41.

Talwar S et al.: Towards a blood test for heart failure: the potential use of circulating natriuretic peptides. J Clin Pharmacol 2000; 50:15-20.

Task Force for the Diagnosis and Treatment of Chronic Heart Failure, European Society of Troughton R W et al.: Treatment of heart failure guided by plasma aminoterminal brain natriuretic peptide (N-BNP) concentrations. Lancet 2000; 355:1126-30.

Yasue H et al.: Localization and mechanism of secretion of B-type natriuretic peptide in comparison with those of A-type natriuretic peptide in normal subjects and patients with heart failure. Circulation 1994; 90: 195-203.

Yoshimura M et al.: Different secretion patterns of atrial natriuretic peptide and brain natriuretic peptide in patients with congestive heart failure. Circulation 1993; 87:464-469.

The invention claimed is:

1. An in vitro method of determining activation or inactivation of the atrial natriuretic peptide (ANP) and brain natriuretic peptide (BNP) hormonal systems in a subject, the method comprising detecting in a single reading, in a single assay the combined presence of atrial and brain natriuretic peptide prohormones (proANP and proBNP) or fragments thereof in a sample from the subject, wherein, compared to a reference level, detection of an increase in the combined presence of proANP and proBNP, or fragments thereof, in the sample indicates activation of the ANP and BNP hormonal systems, and wherein, compared to a reference level, detection of a decrease in the combined presence of proANP and proBNP, or fragments thereof, in the sample indicates inactivation of these systems, wherein said method does not comprise detection of the presence of proANP and proBNP or fragments thereof individually; wherein detection of activation of the ANP and BNP hormonal systems is diagnostic of cardiac impairment or detection of inactivation of ANP and BNP hormonal systems indicates successful treatment of cardiac impairment.

2. The method according to claim 1, which comprises contacting the sample with a bi- or oligo-specific first binding substance that is able to bind to:
   (a) proANP (SEQ ID NO:1), ANP (SEQ ID NO:2), or NT-proANP (SEQ ID NO:3); and
   (b) proBNP (SEQ ID NO:4), BNP (SEQ ID NO:5), or NT-proBNP (SEQ ID NO:6).

3. The method according to claim 1 which comprises contacting the sample with
   a fusion polypeptide agent comprising both:
   (a) proANP (SEQ ID NO:1), ANP (SEQ ID NO:2), or NT-proANP (SEQ ID NO:3);
   and
   (b) proBNP (SEQ ID NO:4), BNP (SEQ ID NO:5), or NT-proBNP (SEQ ID NO:6);
   wherein said fusion polypeptide agent can be bound by a first binding substance, and said fusion polypeptide agent is used as a calibration agent or a competitive inhibitor;
   and
   said first binding substance, which is able to bind to:
   (c) proANP (SEQ ID NO:1), ANP (SEQ ID NO:2), or NT-proANP (SEQ ID NO:3);
   (d) proBNP (SEQ ID NO:4), BNP (SEQ ID NO:5), or NT-proBNP (SEQ ID NO:6); and
   (e) said fusion polypeptide agent.

4. The method according to claim 3 wherein the first binding substance comprises:
   (a) a bi- or oligo-specific binding substance; or
   (b) a mixture of mono-specific binding substances.

5. The method according to claim 2 wherein the first binding substance comprises an antibody or a fragment or derivative thereof, wherein said fragment or derivative thereof retains the binding characteristics of said antibody.

6. The method according to claim 5 wherein the antibody comprises a polyclonal antibody, monoclonal antibody, oligoclonal antibody, bifunctional antibody or crossreacting polyclonal antibody.

7. The method according to claim 3 wherein in the fusion polypeptide agent, (a) is SEQ ID NO:3 and (b) is SEQ ID NO:6, or (a) is SEQ ID NO:2 and (b) is SEQ ID NO:5.

8. The method according to claim 1 which comprises contacting the sample with
a fusion polypeptide agent comprising:
(a) proBNP$_{15-24}$ and proANP$_{82-96}$;
(b) proBNP$_{1-37}$ and proANP$_{29-98}$;
(c) proBNP$_{10-29}$ and proANP$_{20-80}$;
(d) proBNP$_{1-76}$ and proANP$_{1-98}$;
(e) proBNP$_{10-29}$ and proANP$_{60-80}$;
(f) proBNP$_{1-108}$ and proANP$_{1-126}$; or
(g) proBNP$_{77-92}$ and proANP$_{112-126}$;
wherein said fusion polypeptide agent can be bound by a first binding substance, and said fusion polypeptide agent is used as a calibration agent or a competitive inhibitor; and
said first binding substance, which is able to bind to:
(h) proANP (SEQ ID NO:1), ANP (SEQ ID NO:2), or NT-proANP (SEQ ID NO:3); and
(i) proBNP (SEQ ID NO:4), BNP (SEQ ID NO:5), or NT-proBNP (SEQ ID NO:6).

9. The method according to claim 2 wherein the first binding substance and/or the fusion polypeptide agent is:
(a) labelled with a detectable label; and/or
(b) immobilised.

10. The method according to claim 2 which additionally comprises contacting the sample with a second binding substance which is able to bind to the first binding substance.

11. The method according to claim 10 wherein the second binding substance is:
(a) labelled with a detectable label; and/or
(b) immobilised.

12. The method according to claim 10 wherein the second binding substance causes precipitation of the first binding substance and any peptide which is bound to it.

13. The method according to claim 1 which comprises an immunoassay.

14. The method of claim 1, wherein said reference level is determined from a previous measurement from said subject.

15. The method of claim 1, wherein said reference level is based on the normal level of a population of subjects.

16. The method of claim 15, wherein said population of subjects is the general population.

17. The method of claim 1, wherein said assay is calibrated so that a particular reading in the assay is known to represent the normal peptide level.

18. The method of claim 1, wherein said assay is calibrated so that a normal level will produce a negligible or insignificant result.

19. The method of claim 3, wherein said assay is calibrated by use of said fusion polypeptide agent.

20. The method of claim 1, wherein said subject is a human.

* * * * *

SEQUENCE LISTING

```
<160> NUMBER OF SEQ ID NOS: 36

<210> SEQ ID NO 1
<211> LENGTH: 126
<212> TYPE: PRT
<213> ORGANISM: Homo sapiens

<400> SEQUENCE: 1

Asn Pro Met Tyr Asn Ala Val Ser Asn Ala Asp Leu Met Asp Phe Lys
1               5                   10                  15

Asn Leu Leu Asp His Leu Glu Glu Lys Met Pro Leu Glu Asp Glu Val
            20                  25                  30

Val Pro Pro Gln Val Leu Ser Glu Pro Asn Glu Glu Ala Gly Ala Ala
        35                  40                  45

Leu Ser Pro Leu Pro Glu Val Pro Pro Trp Thr Gly Glu Val Ser Pro
    50                  55                  60

Ala Gln Arg Asp Gly Gly Ala Leu Gly Arg Gly Pro Trp Asp Ser Ser
65                  70                  75                  80

Asp Arg Ser Ala Leu Leu Lys Ser Lys Leu Arg Ala Leu Leu Thr Ala
                85                  90                  95

Pro Arg Ser Leu Arg Arg Ser Ser Cys Phe Gly Gly Arg Met Asp Arg
            100                 105                 110

Ile Gly Ala Gln Ser Gly Leu Gly Cys Asn Ser Phe Arg Tyr
        115                 120                 125

<210> SEQ ID NO 2
<211> LENGTH: 28
<212> TYPE: PRT
<213> ORGANISM: Homo sapiens

<400> SEQUENCE: 2

Ser Leu Arg Arg Ser Ser Cys Phe Gly Gly Arg Met Asp Arg Ile Gly
1               5                   10                  15
```

```
Ala Gln Ser Gly Leu Gly Cys Asn Ser Phe Arg Tyr
            20                  25

<210> SEQ ID NO 3
<211> LENGTH: 98
<212> TYPE: PRT
<213> ORGANISM: Homo sapiens

<400> SEQUENCE: 3

Asn Pro Met Tyr Asn Ala Val Ser Asn Ala Asp Leu Met Asp Phe Lys
1               5                   10                  15

Asn Leu Leu Asp His Leu Glu Glu Lys Met Pro Leu Glu Asp Glu Val
            20                  25                  30

Val Pro Pro Gln Val Leu Ser Glu Pro Asn Glu Glu Ala Gly Ala Ala
        35                  40                  45

Leu Ser Pro Leu Pro Glu Val Pro Pro Trp Thr Gly Glu Val Ser Pro
    50                  55                  60

Ala Gln Arg Asp Gly Gly Ala Leu Gly Arg Gly Pro Trp Asp Ser Ser
65                  70                  75                  80

Asp Arg Ser Ala Leu Leu Lys Ser Lys Leu Arg Ala Leu Leu Thr Ala
                85                  90                  95

Pro Arg

<210> SEQ ID NO 4
<211> LENGTH: 108
<212> TYPE: PRT
<213> ORGANISM: Homo sapiens

<400> SEQUENCE: 4

His Pro Leu Gly Ser Pro Gly Ser Ala Ser Asp Leu Glu Thr Ser Gly
1               5                   10                  15

Leu Gln Glu Gln Arg Asn His Leu Gln Gly Lys Leu Ser Glu Leu Gln
            20                  25                  30

Val Glu Gln Thr Ser Leu Glu Pro Leu Gln Glu Ser Pro Arg Pro Thr
        35                  40                  45

Gly Val Trp Lys Ser Arg Glu Val Ala Thr Glu Gly Ile Arg Gly His
    50                  55                  60

Arg Lys Met Val Leu Tyr Thr Leu Arg Ala Pro Arg Ser Pro Lys Met
65                  70                  75                  80

Val Gln Gly Ser Gly Cys Phe Gly Arg Lys Met Asp Arg Ile Ser Ser
                85                  90                  95

Ser Ser Gly Leu Gly Cys Lys Val Leu Arg Arg His
            100                 105

<210> SEQ ID NO 5
<211> LENGTH: 32
<212> TYPE: PRT
<213> ORGANISM: Homo sapiens

<400> SEQUENCE: 5

Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
            20                  25                  30

<210> SEQ ID NO 6
<211> LENGTH: 76
<212> TYPE: PRT
<213> ORGANISM: Homo sapiens
```

<400> SEQUENCE: 6

| His | Pro | Leu | Gly | Ser | Pro | Gly | Ser | Ala | Ser | Asp | Leu | Glu | Thr | Ser | Gly |
| 1   |     |     |     | 5   |     |     |     |     | 10  |     |     |     |     | 15  |     |

| Leu | Gln | Glu | Gln | Arg | Asn | His | Leu | Gln | Gly | Lys | Leu | Ser | Glu | Leu | Gln |
|     |     |     | 20  |     |     |     |     | 25  |     |     |     |     | 30  |     |     |

| Val | Glu | Gln | Thr | Ser | Leu | Glu | Pro | Leu | Gln | Glu | Ser | Pro | Arg | Pro | Thr |
|     |     |     | 35  |     |     |     |     | 40  |     |     |     |     | 45  |     |     |

| Gly | Val | Trp | Lys | Ser | Arg | Glu | Val | Ala | Thr | Glu | Gly | Ile | Arg | Gly | His |
|     |     |     | 50  |     |     |     |     | 55  |     |     |     |     | 60  |     |     |

| Arg | Lys | Met | Val | Leu | Tyr | Thr | Leu | Arg | Ala | Pro | Arg |
| 65  |     |     |     | 70  |     |     |     |     | 75  |     |     |

<210> SEQ ID NO 7
<211> LENGTH: 378
<212> TYPE: DNA
<213> ORGANISM: Homo sapiens

<400> SEQUENCE: 7

```
aatcccatgt acaatgccgt gtccaacgca gacctgatgg atttcaagaa tttgctggac      60
catttggaag aaaagatgcc tttagaagat gaggtcgtgc ccccacaagt gctcagtgag     120
ccgaatgaag aagcggggc tgctctcagc ccctcctg aggtgcctcc ctggaccggg         180
gaagtcagcc cagcccagag agatggaggt gccctcgggc ggggcccctg ggactcctct     240
gatcgatctg ccctcctaaa aagcaagctg agggcgctgc tcactgcccc tcggagcctg     300
cggagatcca gctgcttcgg gggcaggatg gacaggattg agcccagag cggactgggc       360
tgtaacagct tccggtac                                                    378
```

<210> SEQ ID NO 8
<211> LENGTH: 84
<212> TYPE: DNA
<213> ORGANISM: Homo sapiens

<400> SEQUENCE: 8

```
agcctgcgga gatccagctg cttcggggc aggatggaca ggattggagc ccagagcgga      60
ctgggctgta acagcttccg gtac                                             84
```

<210> SEQ ID NO 9
<211> LENGTH: 294
<212> TYPE: DNA
<213> ORGANISM: Homo sapiens

<400> SEQUENCE: 9

```
aatcccatgt acaatgccgt gtccaacgca gacctgatgg atttcaagaa tttgctggac      60
catttggaag aaaagatgcc tttagaagat gaggtcgtgc ccccacaagt gctcagtgag     120
ccgaatgaag aagcggggc tgctctcagc ccctcctg aggtgcctcc ctggaccggg         180
gaagtcagcc cagcccagag agatggaggt gccctcgggc ggggcccctg ggactcctct     240
gatcgatctg ccctcctaaa aagcaagctg agggcgctgc tcactgcccc tcgg           294
```

<210> SEQ ID NO 10
<211> LENGTH: 324
<212> TYPE: DNA
<213> ORGANISM: Homo sapiens

<400> SEQUENCE: 10

```
cacccgctgg gcagccccgg ttcagcctcg gacttggaaa cgtccgggtt acaggagcag      60
```

```
cgcaaccatt tgcagggcaa actgtcggag ctgcaggtgg agcagacatc cctggagccc    120
ctccaggaga gcccccgtcc cacaggtgtc tggaagtccc gggaggtagc caccgagggc    180
atccgtgggc accgcaaaat ggtcctctac accctgcggg caccacgaag ccccaagatg    240
gtgcaagggt ctggctgctt tgggaggaag atggaccgga tcagctcctc cagtggcctg    300
ggctgcaaag tgctgaggcg gcat                                           324

<210> SEQ ID NO 11
<211> LENGTH: 96
<212> TYPE: DNA
<213> ORGANISM: Homo sapiens

<400> SEQUENCE: 11
agccccaaga tggtgcaagg gtctggctgc tttgggagga agatggaccg gatcagctcc     60
tccagtggcc tgggctgcaa agtgctgagg cggcat                               96

<210> SEQ ID NO 12
<211> LENGTH: 228
<212> TYPE: DNA
<213> ORGANISM: Homo sapiens

<400> SEQUENCE: 12
cacccgctgg gcagcccgg ttcagcctcg gacttggaaa cgtccgggtt acaggagcag      60
cgcaaccatt tgcagggcaa actgtcggag ctgcaggtgg agcagacatc cctggagccc    120
ctccaggaga gcccccgtcc cacaggtgtc tggaagtccc gggaggtagc caccgagggc    180
atccgtgggc accgcaaaat ggtcctctac accctgcggg caccacga                 228

<210> SEQ ID NO 13
<211> LENGTH: 25
<212> TYPE: PRT
<213> ORGANISM: Artificial sequence
<220> FEATURE:
<223> OTHER INFORMATION: Synthetic peptide

<400> SEQUENCE: 13

Ser Gly Leu Gln Glu Gln Arg Asn His Leu Arg Ser Ala Leu Leu Lys
1               5                   10                  15

Ser Lys Leu Arg Ala Leu Leu Thr Ala
            20                  25

<210> SEQ ID NO 14
<211> LENGTH: 107
<212> TYPE: PRT
<213> ORGANISM: Artificial sequence
<220> FEATURE:
<223> OTHER INFORMATION: Synthetic peptide

<400> SEQUENCE: 14

His Pro Leu Gly Ser Pro Gly Ser Ala Ser Asp Leu Glu Thr Ser Gly
1               5                   10                  15

Leu Gln Glu Gln Arg Asn His Leu Gln Gly Lys Leu Ser Glu Leu Gln
                20                  25                  30

Val Glu Gln Thr Ser Glu Asp Glu Val Val Pro Gln Val Leu Ser
                35                  40              45

Glu Pro Asn Glu Glu Ala Gly Ala Ala Leu Ser Pro Leu Pro Glu Val
        50                  55                  60

Pro Pro Trp Thr Gly Glu Val Ser Pro Ala Gln Arg Asp Gly Ala
65                  70                  75              80

Leu Gly Arg Gly Pro Trp Asp Ser Ser Asp Arg Ser Ala Leu Leu Lys
```

```
                    85                  90                  95

Ser Lys Leu Arg Ala Leu Leu Thr Ala Pro Arg
                100                 105

<210> SEQ ID NO 15
<211> LENGTH: 81
<212> TYPE: PRT
<213> ORGANISM: Artificial sequence
<220> FEATURE:
<223> OTHER INFORMATION: Synthetic peptide

<400> SEQUENCE: 15

Ser Asp Leu Glu Thr Ser Gly Leu Gln Glu Gln Arg Asn His Leu Gln
1               5                   10                  15

Gly Lys Leu Ser Asp His Leu Glu Glu Lys Met Pro Leu Glu Asp Glu
            20                  25                  30

Val Val Pro Pro Gln Val Leu Ser Glu Pro Asn Glu Glu Ala Gly Ala
        35                  40                  45

Ala Leu Ser Pro Leu Pro Glu Val Pro Pro Trp Thr Gly Glu Val Ser
    50                  55                  60

Pro Ala Gln Arg Asp Gly Gly Ala Leu Gly Arg Gly Pro Trp Asp Ser
65                  70                  75                  80

Ser

<210> SEQ ID NO 16
<211> LENGTH: 4
<212> TYPE: PRT
<213> ORGANISM: Artificial sequence
<220> FEATURE:
<223> OTHER INFORMATION: Synthetic peptide

<400> SEQUENCE: 16

Gly Lys Tyr Gly
1

<210> SEQ ID NO 17
<211> LENGTH: 174
<212> TYPE: PRT
<213> ORGANISM: Artificial sequence
<220> FEATURE:
<223> OTHER INFORMATION: Synthetic peptide

<400> SEQUENCE: 17

His Pro Leu Gly Ser Pro Gly Ser Ala Ser Asp Leu Glu Thr Ser Gly
1               5                   10                  15

Leu Gln Glu Gln Arg Asn His Leu Gln Gly Lys Leu Ser Glu Leu Gln
            20                  25                  30

Val Glu Gln Thr Ser Leu Glu Pro Leu Gln Glu Ser Pro Arg Pro Thr
        35                  40                  45

Gly Val Trp Lys Ser Arg Glu Val Ala Thr Glu Gly Ile Arg Gly His
    50                  55                  60

Arg Lys Met Val Leu Tyr Thr Leu Arg Ala Pro Arg Asn Pro Met Tyr
65                  70                  75                  80

Asn Ala Val Ser Asn Ala Asp Leu Met Asp Phe Lys Asn Leu Leu Asp
                85                  90                  95

His Leu Glu Glu Lys Met Pro Leu Glu Asp Val Val Pro Pro Gln
                100                 105                 110

Val Leu Ser Glu Pro Asn Glu Glu Ala Gly Ala Ala Leu Ser Pro Leu
            115                 120                 125

Pro Glu Val Pro Pro Trp Thr Gly Glu Val Ser Pro Ala Gln Arg Asp
```

```
                130                 135                 140
Gly Gly Ala Leu Gly Arg Gly Pro Trp Asp Ser Ser Asp Arg Ser Ala
145                 150                 155                 160

Leu Leu Lys Ser Lys Leu Arg Ala Leu Leu Thr Ala Pro Arg
                165                 170
```

```
<210> SEQ ID NO 18
<211> LENGTH: 41
<212> TYPE: PRT
<213> ORGANISM: Artificial sequence
<220> FEATURE:
<223> OTHER INFORMATION: Synthetic peptide

<400> SEQUENCE: 18

Ser Asp Leu Glu Thr Ser Gly Leu Gln Glu Gln Arg Asn His Leu Gln
1               5                   10                  15

Gly Lys Leu Ser Gly Glu Val Ser Pro Ala Gln Arg Asp Gly Gly Ala
                20                  25                  30

Leu Gly Arg Gly Pro Trp Asp Ser Ser
            35                  40
```

```
<210> SEQ ID NO 19
<211> LENGTH: 234
<212> TYPE: PRT
<213> ORGANISM: Artificial sequence
<220> FEATURE:
<223> OTHER INFORMATION: Synthetic peptide

<400> SEQUENCE: 19

His Pro Leu Gly Ser Pro Gly Ser Ala Ser Asp Leu Glu Thr Ser Gly
1               5                   10                  15

Leu Gln Glu Gln Arg Asn His Leu Gln Gly Lys Leu Ser Glu Leu Gln
                20                  25                  30

Val Glu Gln Thr Ser Leu Glu Pro Leu Gln Glu Ser Pro Arg Pro Thr
            35                  40                  45

Gly Val Trp Lys Ser Arg Glu Val Ala Thr Glu Gly Ile Arg Gly His
        50                  55                  60

Arg Lys Met Val Leu Tyr Thr Leu Arg Ala Pro Arg Ser Pro Lys Met
65                  70                  75                  80

Val Gln Gly Ser Gly Cys Phe Gly Arg Lys Met Asp Arg Ile Ser Ser
                85                  90                  95

Ser Ser Gly Leu Gly Cys Lys Val Leu Arg Arg His Asn Pro Met Tyr
                100                 105                 110

Asn Ala Val Ser Asn Ala Asp Leu Met Asp Phe Lys Asn Leu Leu Asp
            115                 120                 125

His Leu Glu Glu Lys Met Pro Leu Glu Asp Glu Val Val Pro Pro Gln
        130                 135                 140

Val Leu Ser Glu Pro Asn Glu Glu Ala Gly Ala Ala Leu Ser Pro Leu
145                 150                 155                 160

Pro Glu Val Pro Pro Trp Thr Gly Glu Val Ser Pro Ala Gln Arg Asp
                165                 170                 175

Gly Gly Ala Leu Gly Arg Gly Pro Trp Asp Ser Ser Asp Arg Ser Ala
            180                 185                 190

Leu Leu Lys Ser Lys Leu Arg Ala Leu Leu Thr Ala Pro Arg Ser Leu
        195                 200                 205

Arg Arg Ser Ser Cys Phe Gly Gly Arg Met Asp Arg Ile Gly Ala Gln
210                 215                 220

Ser Gly Leu Gly Cys Asn Ser Phe Arg Tyr
```

```
225              230

<210> SEQ ID NO 20
<211> LENGTH: 31
<212> TYPE: PRT
<213> ORGANISM: Artificial sequence
<220> FEATURE:
<223> OTHER INFORMATION: Synthetic peptide

<400> SEQUENCE: 20

Ser Pro Lys Met Val Gln Gly Ser Gly Cys Phe Gly Arg Lys Met Asp
1               5                   10                  15

Arg Ile Gly Ala Gln Ser Gly Leu Gly Cys Asn Ser Phe Arg Tyr
            20                  25                  30

<210> SEQ ID NO 21
<211> LENGTH: 75
<212> TYPE: DNA
<213> ORGANISM: Artificial sequence
<220> FEATURE:
<223> OTHER INFORMATION: Synthetic nucleic acid

<400> SEQUENCE: 21
tccgggttac aggagcagcg caaccatttg cgatctgccc tcctaaaaag caagctgagg      60
gcgctgctca ctgcc                                                      75

<210> SEQ ID NO 22
<211> LENGTH: 321
<212> TYPE: DNA
<213> ORGANISM: Artificial sequence
<220> FEATURE:
<223> OTHER INFORMATION: Synthetic nucleic acid

<400> SEQUENCE: 22
cacccgctgg gcagccccgg ttcagcctcg gacttggaaa cgtccggggtt acaggagcag    60 cgcaaccatt tgcagggcaa actgtcggag ctgcaggtgg agcagacatc cgaagatgag    120
gtcgtgcccc acaagtgct cagtgagccg aatgaagaag cggggggctgc tctcagcccc    180 ctccctgagg tgcctcccctg gaccggggaa gtcagcccag cccagagaga tggaggtgcc   240
ctcgggcggg gccctggga ctcctctgat cgatctgccc tcctaaaaag caagctgagg    300
gcgctgctca ctgcccctcg g                                              321

<210> SEQ ID NO 23
<211> LENGTH: 241
<212> TYPE: DNA
<213> ORGANISM: Artificial sequence
<220> FEATURE:
<223> OTHER INFORMATION: Synthetic nucleic acid

<400> SEQUENCE: 23
tcggacttgg aaacgtccgg gttacaggag cagcgcaacc atttgcaggg caaactgtga    60
ccatttggaa gaaaagatgc ctttagaaga tgaggtcgtg ccccacaag tgctcagtga    120 gccgaatgaa gaagcggggg ctgctctcag cccctccct gaggtgcctc cctggaccgg    180
ggaagtcagc ccagcccaga gagatggagg tgccctcggg cggggcccct gggactcctc   240
t                                                                    241

<210> SEQ ID NO 24
<211> LENGTH: 522
<212> TYPE: DNA
<213> ORGANISM: Artificial sequence
<220> FEATURE:
```

<223> OTHER INFORMATION: Synthetic nucleic acid

<400> SEQUENCE: 24

```
cacccgctgg gcagccccgg ttcagcctcg gacttggaaa cgtccgggtt acaggagcag      60
cgcaaccatt tgcagggcaa actgtcggag ctgcaggtgg agcagacatc cctggagccc     120
ctccaggaga gcccccgtcc cacaggtgtc tggaagtccc gggaggtagc caccgagggc     180
atccgtgggc accgcaaaat ggtcctctac accctgcggg caccacgaaa tcccatgtac     240
aatgccgtgt ccaacgcaga cctgatggat ttcaagaatt tgctggacca tttggaagaa     300
aagatgcctt tagaagatga ggtcgtgccc ccacaagtgc tcagtgagcc gaatgaagaa     360
gcgggggctg ctctcagccc cctccctgag gtgcctccct ggaccgggga agtcagccca     420
gcccagagag atggaggtgc cctgggcgg ggccctggg actcctctga tcgatctgcc       480
ctcctaaaaa gcaagctgag ggcgctgctc actgcccctc gg                        522
```

<210> SEQ ID NO 25
<211> LENGTH: 123
<212> TYPE: DNA
<213> ORGANISM: Artificial sequence
<220> FEATURE:
<223> OTHER INFORMATION: Synthetic nucleic acid

<400> SEQUENCE: 25

```
tcggacttgg aaacgtccgg gttacaggag cagcgcaacc atttgcaggg caaactgtcg      60
ggggaagtca gcccagccca gagagatgga ggtgccctcg gcggggccc ctgggactcc      120
tct                                                                   123
```

<210> SEQ ID NO 26
<211> LENGTH: 702
<212> TYPE: DNA
<213> ORGANISM: Artificial sequence
<220> FEATURE:
<223> OTHER INFORMATION: Synthetic nucleic acid

<400> SEQUENCE: 26

```
cacccgctgg gcagccccgg ttcagcctcg gacttggaaa cgtccgggtt acaggagcag      60
cgcaaccatt tgcagggcaa actgtcggag ctgcaggtgg agcagacatc cctggagccc     120
ctccaggaga gcccccgtcc cacaggtgtc tggaagtccc gggaggtagc caccgagggc     180
atccgtgggc accgcaaaat ggtcctctac accctgcggg caccacgaag ccccaagatg     240
gtgcaagggt ctggctgctt tgggaggaag atggaccgga tcagctcctc cagtggcctg     300
ggctgcaaag tgctgaggcg gcataatccc atgtacaatg ccgtgtccaa cgcagacctg     360
atggatttca agaatttgct ggaccatttg aagaaaaga tgcctttaga agatgaggtc      420
gtgcccccac aagtgctcag tgagccgaat gaagaagcgg gggctgctct cagcccctc     480
cctgaggtgc ctccctggac cggggaagtc agcccagccc agagagatgg aggtgccctc    540
ggcgggcc cctgggactc ctctgatcga tctgccctcc taaaaagcaa gctgagggcg      600
ctgctcactg cccctcggag cctgcggaga tccagctgct cgggggcag gatggacagg      660
attggagccc agagcggact gggctgtaac agcttccggt ac                        702
```

<210> SEQ ID NO 27
<211> LENGTH: 93
<212> TYPE: DNA
<213> ORGANISM: Artificial sequence
<220> FEATURE:
<223> OTHER INFORMATION: Synthetic nucleic acid

```
<400> SEQUENCE: 27
agccccaaga tggtgcaagg gtctggctgc tttgggagga agatggacag gattggagcc    60
cagagcggac tgggctgtaa cagcttccgg tac                                 93

<210> SEQ ID NO 28
<211> LENGTH: 27
<212> TYPE: DNA
<213> ORGANISM: Artificial sequence
<220> FEATURE:
<223> OTHER INFORMATION: Primer

<400> SEQUENCE: 28
gcggatccca cccgctgggc agcccg                                         27

<210> SEQ ID NO 29
<211> LENGTH: 24
<212> TYPE: DNA
<213> ORGANISM: Artificial sequence
<220> FEATURE:
<223> OTHER INFORMATION: Primer

<400> SEQUENCE: 29
gctctagagg atgtctgctc cacc                                           24

<210> SEQ ID NO 30
<211> LENGTH: 24
<212> TYPE: DNA
<213> ORGANISM: Artificial sequence
<220> FEATURE:
<223> OTHER INFORMATION: Primer

<400> SEQUENCE: 30
gctctagaga agatgaggtc gtgc                                           24

<210> SEQ ID NO 31
<211> LENGTH: 27
<212> TYPE: DNA
<213> ORGANISM: Artificial sequence
<220> FEATURE:
<223> OTHER INFORMATION: Primer

<400> SEQUENCE: 31
gcgaattctc accgaggggc agtgagc                                        27

<210> SEQ ID NO 32
<211> LENGTH: 25
<212> TYPE: DNA
<213> ORGANISM: Artificial sequence
<220> FEATURE:
<223> OTHER INFORMATION: Primer

<400> SEQUENCE: 32
gcggatccta ccacccgctg ggcag                                          25

<210> SEQ ID NO 33
<211> LENGTH: 1061
<212> TYPE: PRT
<213> ORGANISM: Homo sapiens

<400> SEQUENCE: 33

Met Pro Gly Pro Arg Arg Pro Ala Gly Ser Arg Leu Arg Leu Leu Leu
1               5                   10                  15

Leu Leu Leu Leu Pro Pro Leu Leu Leu Leu Arg Gly Ser His Ala
            20                  25                  30
```

```
Gly Asn Leu Thr Val Ala Val Leu Pro Leu Ala Asn Thr Ser Tyr
            35                  40                  45
Pro Trp Ser Trp Ala Arg Val Gly Pro Ala Val Glu Leu Ala Leu Ala
 50                  55                  60
Gln Val Lys Ala Arg Pro Asp Leu Leu Pro Gly Trp Thr Val Arg Thr
 65                  70                  75                  80
Val Leu Gly Ser Ser Glu Asn Ala Leu Gly Val Cys Ser Asp Thr Ala
                 85                  90                  95
Ala Pro Leu Ala Ala Val Asp Leu Lys Trp Glu His Asn Pro Ala Val
                100                 105                 110
Phe Leu Gly Pro Gly Cys Val Tyr Ala Ala Pro Val Gly Arg Phe
                115                 120                 125
Thr Ala His Trp Arg Val Pro Leu Leu Thr Ala Gly Ala Pro Ala Leu
    130                 135                 140
Gly Phe Gly Val Lys Asp Glu Tyr Ala Leu Thr Thr Arg Ala Gly Pro
145                 150                 155                 160
Ser Tyr Ala Lys Leu Gly Asp Phe Val Ala Ala Leu His Arg Arg Leu
                165                 170                 175
Gly Trp Glu Arg Gln Ala Leu Met Leu Tyr Ala Tyr Arg Pro Gly Asp
                180                 185                 190
Glu Glu His Cys Phe Phe Leu Val Glu Gly Leu Phe Met Arg Val Arg
                195                 200                 205
Asp Arg Leu Asn Ile Thr Val Asp His Leu Glu Phe Ala Glu Asp Asp
    210                 215                 220
Leu Ser His Tyr Thr Arg Leu Leu Arg Thr Met Pro Arg Lys Gly Arg
225                 230                 235                 240
Val Ile Tyr Ile Cys Ser Ser Pro Asp Ala Phe Arg Thr Leu Met Leu
                245                 250                 255
Leu Ala Leu Glu Ala Gly Leu Cys Gly Glu Asp Tyr Val Phe Phe His
                260                 265                 270
Leu Asp Ile Phe Gly Gln Ser Leu Gln Gly Gln Gly Pro Ala Pro
    275                 280                 285
Arg Arg Pro Trp Glu Arg Gly Asp Gly Gln Asp Val Ser Ala Arg Gln
290                 295                 300
Ala Phe Gln Ala Ala Lys Ile Ile Thr Tyr Lys Asp Pro Asp Asn Pro
305                 310                 315                 320
Glu Tyr Leu Glu Phe Leu Lys Gln Leu Lys His Leu Ala Tyr Glu Gln
                325                 330                 335
Phe Asn Phe Thr Met Glu Asp Gly Leu Val Asn Thr Ile Pro Ala Ser
                340                 345                 350
Phe His Asp Gly Leu Leu Leu Tyr Ile Gln Ala Val Thr Glu Thr Leu
                355                 360                 365
Ala His Gly Gly Thr Val Thr Asp Gly Glu Asn Ile Thr Gln Arg Met
    370                 375                 380
Trp Asn Arg Ser Phe Gln Gly Val Thr Gly Tyr Leu Lys Ile Asp Ser
385                 390                 395                 400
Ser Gly Asp Arg Glu Thr Asp Phe Ser Leu Trp Asp Met Asp Pro Glu
                405                 410                 415
Asn Gly Ala Phe Arg Val Val Leu Asn Tyr Asn Gly Thr Ser Gln Glu
                420                 425                 430
Leu Val Ala Val Ser Gly Arg Lys Leu Asn Trp Pro Leu Gly Tyr Pro
    435                 440                 445
Pro Pro Asp Ile Pro Lys Cys Gly Phe Asp Asn Glu Asp Pro Ala Cys
450                 455                 460
```

```
Asn Gln Asp His Leu Ser Thr Leu Glu Val Leu Ala Leu Val Gly Ser
465                 470                 475                 480

Leu Ser Leu Leu Gly Ile Leu Ile Val Ser Phe Phe Ile Tyr Arg Lys
                485                 490                 495

Met Gln Leu Glu Lys Glu Leu Ala Ser Glu Leu Trp Arg Val Arg Trp
            500                 505                 510

Glu Asp Val Glu Pro Ser Ser Leu Glu Arg His Leu Arg Ser Ala Gly
            515                 520                 525

Ser Arg Leu Thr Leu Ser Gly Arg Gly Ser Asn Tyr Gly Ser Leu Leu
        530                 535                 540

Thr Thr Glu Gly Gln Phe Gln Val Phe Ala Lys Thr Ala Tyr Tyr Lys
545                 550                 555                 560

Gly Asn Leu Val Ala Val Lys Arg Val Asn Arg Lys Arg Ile Glu Leu
                565                 570                 575

Thr Arg Lys Val Leu Phe Glu Leu Lys His Met Arg Asp Val Gln Asn
            580                 585                 590

Glu His Leu Thr Arg Phe Val Gly Ala Cys Thr Asp Pro Pro Asn Ile
        595                 600                 605

Cys Ile Leu Thr Glu Tyr Cys Pro Arg Gly Ser Leu Gln Asp Ile Leu
610                 615                 620

Glu Asn Glu Ser Ile Thr Leu Asp Trp Met Phe Arg Tyr Ser Leu Thr
625                 630                 635                 640

Asn Asp Ile Val Lys Gly Met Leu Phe Leu His Asn Gly Ala Ile Cys
                645                 650                 655

Ser His Gly Asn Leu Lys Ser Ser Asn Cys Val Val Asp Gly Arg Phe
            660                 665                 670

Val Leu Lys Ile Thr Asp Tyr Gly Leu Glu Ser Phe Arg Asp Leu Asp
            675                 680                 685

Pro Glu Gln Gly His Thr Val Tyr Ala Lys Lys Leu Trp Thr Ala Pro
690                 695                 700

Glu Leu Leu Arg Met Ala Ser Pro Pro Val Arg Gly Ser Gln Ala Gly
705                 710                 715                 720

Asp Val Tyr Ser Phe Gly Ile Ile Leu Gln Glu Ile Ala Leu Arg Ser
                725                 730                 735

Gly Val Phe His Val Glu Gly Leu Asp Leu Ser Pro Lys Glu Ile Ile
            740                 745                 750

Glu Arg Val Thr Arg Gly Glu Gln Pro Pro Phe Arg Pro Ser Leu Ala
            755                 760                 765

Leu Gln Ser His Leu Glu Glu Leu Gly Leu Leu Met Gln Arg Cys Trp
        770                 775                 780

Ala Glu Asp Pro Gln Glu Arg Pro Pro Phe Gln Gln Ile Arg Leu Thr
785                 790                 795                 800

Leu Arg Lys Phe Asn Arg Glu Asn Ser Ser Asn Ile Leu Asp Asn Leu
                805                 810                 815

Leu Ser Arg Met Glu Gln Tyr Ala Asn Asn Leu Glu Glu Leu Val Glu
            820                 825                 830

Glu Arg Thr Gln Ala Tyr Leu Glu Glu Lys Arg Lys Ala Glu Ala Leu
            835                 840                 845

Leu Tyr Gln Ile Leu Pro His Ser Val Ala Glu Gln Leu Lys Arg Gly
        850                 855                 860

Glu Thr Val Gln Ala Glu Ala Phe Asp Ser Val Thr Ile Tyr Phe Ser
865                 870                 875                 880

Asp Ile Val Gly Phe Thr Ala Leu Ser Ala Glu Ser Thr Pro Met Gln
```

```
                       885                 890                 895
Val Val Thr Leu Leu Asn Asp Leu Tyr Thr Cys Phe Asp Ala Val Ile
                900                 905                 910

Asp Asn Phe Asp Val Tyr Lys Val Glu Thr Ile Gly Asp Ala Tyr Met
            915                 920                 925

Val Val Ser Gly Leu Pro Val Arg Asn Gly Arg Leu His Ala Cys Glu
        930                 935                 940

Val Ala Arg Met Ala Leu Ala Leu Leu Asp Ala Val Arg Ser Phe Arg
945                 950                 955                 960

Ile Arg His Arg Pro Gln Glu Gln Leu Arg Leu Arg Ile Gly Ile His
                965                 970                 975

Thr Gly Pro Val Cys Ala Gly Val Val Gly Leu Lys Met Pro Arg Tyr
            980                 985                 990

Cys Leu Phe Gly Asp Thr Val Asn  Thr Ala Ser Arg Met  Glu Ser Asn
        995                 1000                1005

Gly Glu  Ala Leu Lys Ile His  Leu Ser Ser Glu Thr  Lys Ala Val
    1010                 1015                1020

Leu Glu  Glu Phe Gly Gly Phe  Glu Leu Glu Leu Arg  Gly Asp Val
    1025                 1030                1035

Glu Met  Lys Gly Lys Gly Lys  Val Arg Thr Tyr Trp  Leu Leu Gly
    1040                 1045                1050

Glu Arg  Gly Ser Ser Thr Arg  Gly
    1055                 1060

<210> SEQ ID NO 34
<211> LENGTH: 430
<212> TYPE: PRT
<213> ORGANISM: Homo sapiens

<400> SEQUENCE: 34

Gly Asn Leu Thr Val Ala Val Val Leu Pro Leu Ala Asn Thr Ser Tyr
1               5                   10                  15

Pro Trp Ser Trp Ala Arg Val Gly Pro Ala Val Glu Leu Ala Leu Ala
            20                  25                  30

Gln Val Lys Ala Arg Pro Asp Leu Leu Pro Gly Trp Thr Val Arg Thr
        35                  40                  45

Val Leu Gly Ser Ser Glu Asn Ala Leu Gly Val Cys Ser Asp Thr Ala
    50                  55                  60

Ala Pro Leu Ala Ala Val Asp Leu Lys Trp Glu His Asn Pro Ala Val
65                  70                  75                  80

Phe Leu Gly Pro Gly Cys Val Tyr Ala Ala Ala Pro Val Gly Arg Phe
                85                  90                  95

Thr Ala His Trp Arg Val Pro Leu Leu Thr Ala Gly Ala Pro Ala Leu
            100                 105                 110

Gly Phe Gly Val Lys Asp Glu Tyr Ala Leu Thr Thr Arg Ala Gly Pro
        115                 120                 125

Ser Tyr Ala Lys Leu Gly Asp Phe Val Ala Leu His Arg Arg Leu
    130                 135                 140

Gly Trp Glu Arg Gln Ala Leu Met Leu Tyr Ala Tyr Arg Pro Gly Asp
145                 150                 155                 160

Glu Glu His Cys Phe Phe Leu Val Glu Gly Leu Phe Met Arg Val Arg
                165                 170                 175

Asp Arg Leu Asn Ile Thr Val Asp His Leu Glu Phe Ala Glu Asp Asp
            180                 185                 190

Leu Ser His Tyr Thr Arg Leu Leu Arg Thr Met Pro Arg Lys Gly Arg
```

```
                195                 200                 205
Val Ile Tyr Ile Cys Ser Ser Pro Asp Ala Phe Arg Thr Leu Met Leu
210                 215                 220

Leu Ala Leu Glu Ala Gly Leu Cys Gly Glu Asp Tyr Val Phe Phe His
225                 230                 235                 240

Leu Asp Ile Phe Gly Gln Ser Leu Gln Gly Gln Gly Pro Ala Pro
                245                 250                 255

Arg Arg Pro Trp Glu Arg Gly Asp Gln Asp Val Ser Ala Arg Gln
                260                 265                 270

Ala Phe Gln Ala Ala Lys Ile Ile Thr Tyr Lys Asp Pro Asp Asn Pro
                275                 280                 285

Glu Tyr Leu Glu Phe Leu Lys Gln Leu Lys His Leu Ala Tyr Glu Gln
                290                 295                 300

Phe Asn Phe Thr Met Glu Asp Gly Leu Val Asn Thr Ile Pro Ala Ser
305                 310                 315                 320

Phe His Asp Gly Leu Leu Tyr Ile Gln Ala Val Thr Glu Thr Leu
                325                 330                 335

Ala His Gly Gly Thr Val Thr Asp Gly Glu Asn Ile Thr Gln Arg Met
                340                 345                 350

Trp Asn Arg Ser Phe Gln Gly Val Thr Gly Tyr Leu Lys Ile Asp Ser
                355                 360                 365

Ser Gly Asp Arg Glu Thr Asp Phe Ser Leu Trp Asp Met Asp Pro Glu
                370                 375                 380

Asn Gly Ala Phe Arg Val Val Leu Asn Tyr Asn Gly Thr Ser Gln Glu
385                 390                 395                 400

Leu Val Ala Val Ser Gly Arg Lys Leu Asn Trp Pro Leu Gly Tyr Pro
                405                 410                 415

Pro Pro Asp Ile Pro Lys Cys Gly Phe Asp Asn Glu Asp Pro
                420                 425                 430

<210> SEQ ID NO 35
<211> LENGTH: 1047
<212> TYPE: PRT
<213> ORGANISM: Homo sapiens

<400> SEQUENCE: 35

Met Ala Leu Pro Ser Leu Leu Leu Leu Val Ala Ala Leu Ala Gly Gly
1               5                   10                  15

Val Arg Pro Pro Gly Ala Arg Asn Leu Thr Leu Ala Val Val Leu Pro
                20                  25                  30

Glu His Asn Leu Ser Tyr Ala Trp Ala Trp Pro Arg Val Gly Pro Ala
                35                  40                  45

Val Ala Leu Ala Val Glu Ala Leu Gly Arg Ala Leu Pro Val Asp Leu
                50                  55                  60

Arg Phe Val Ser Ser Glu Leu Glu Gly Ala Cys Ser Glu Tyr Leu Ala
65                  70                  75                  80

Pro Leu Ser Ala Val Asp Leu Lys Leu Tyr His Asp Pro Asp Leu Leu
                85                  90                  95

Leu Gly Pro Gly Cys Val Tyr Pro Ala Ala Ser Val Ala Arg Phe Ala
                100                 105                 110

Ser His Trp Arg Leu Pro Leu Leu Thr Ala Gly Ala Val Ala Ser Gly
                115                 120                 125

Phe Ser Ala Lys Asn Asp His Tyr Arg Thr Leu Val Arg Thr Gly Pro
                130                 135                 140

Ser Ala Pro Lys Leu Gly Glu Phe Val Val Thr Leu His Gly His Phe
```

-continued

```
            145                 150                 155                 160
Asn Trp Thr Ala Arg Ala Ala Leu Leu Tyr Leu Asp Ala Arg Thr Asp
                165                 170                 175
Asp Arg Pro His Tyr Phe Thr Ile Glu Gly Val Phe Glu Ala Leu Gln
                180                 185                 190
Gly Ser Asn Leu Ser Val Gln His Gln Val Tyr Ala Arg Glu Pro Gly
                195                 200                 205
Gly Pro Glu Gln Ala Thr His Phe Ile Arg Ala Asn Gly Arg Ile Val
                210                 215                 220
Tyr Ile Cys Gly Pro Leu Glu Met Leu His Glu Ile Leu Leu Gln Ala
225                 230                 235                 240
Gln Arg Glu Asn Leu Thr Asn Gly Asp Tyr Val Phe Phe Tyr Leu Asp
                245                 250                 255
Val Phe Gly Glu Ser Leu Arg Ala Gly Pro Thr Arg Ala Thr Gly Arg
                260                 265                 270
Pro Trp Gln Asp Asn Arg Thr Arg Glu Gln Ala Gln Ala Leu Arg Glu
                275                 280                 285
Ala Phe Gln Thr Val Leu Val Ile Thr Tyr Arg Glu Pro Pro Asn Pro
                290                 295                 300
Glu Tyr Gln Glu Phe Gln Asn Arg Leu Leu Ile Arg Ala Arg Glu Asp
305                 310                 315                 320
Phe Gly Val Glu Leu Gly Pro Ser Leu Met Asn Leu Ile Ala Gly Cys
                325                 330                 335
Phe Tyr Asp Gly Ile Leu Leu Tyr Ala Glu Val Leu Asn Glu Thr Ile
                340                 345                 350
Gln Glu Gly Gly Thr Arg Glu Asp Gly Leu Arg Ile Val Glu Lys Met
                355                 360                 365
Gln Gly Arg Arg Tyr His Gly Val Thr Gly Leu Val Val Met Asp Lys
                370                 375                 380
Asn Asn Asp Arg Glu Thr Asp Phe Val Leu Trp Ala Met Gly Asp Leu
385                 390                 395                 400
Asp Ser Gly Asp Phe Gln Pro Ala Ala His Tyr Ser Gly Ala Glu Lys
                405                 410                 415
Gln Ile Trp Trp Thr Gly Arg Pro Ile Pro Trp Val Lys Gly Ala Pro
                420                 425                 430
Pro Ser Asp Asn Pro Pro Cys Ala Phe Asp Leu Asp Pro Ser Cys
                435                 440                 445
Asp Lys Thr Pro Leu Ser Thr Leu Ala Ile Val Ala Leu Gly Thr Gly
                450                 455                 460
Ile Thr Phe Ile Met Phe Gly Val Ser Ser Phe Leu Ile Phe Arg Lys
465                 470                 475                 480
Leu Met Leu Glu Lys Glu Leu Ala Ser Met Leu Trp Arg Ile Arg Trp
                485                 490                 495
Glu Glu Leu Gln Phe Gly Asn Ser Glu Arg Tyr His Lys Gly Ala Gly
                500                 505                 510
Ser Arg Leu Thr Leu Ser Leu Arg Gly Ser Ser Tyr Gly Ser Leu Met
                515                 520                 525
Thr Ala His Gly Lys Tyr Gln Ile Phe Ala Asn Thr Gly His Phe Lys
                530                 535                 540
Gly Asn Val Val Ala Ile Lys His Val Asn Lys Lys Arg Ile Glu Leu
545                 550                 555                 560
Thr Arg Gln Val Leu Phe Glu Leu Lys His Met Arg Asp Val Gln Phe
                565                 570                 575
```

```
-continued

Asn His Leu Thr Arg Phe Ile Gly Ala Cys Ile Asp Pro Asn Ile
            580                 585                 590

Cys Ile Val Thr Glu Tyr Cys Pro Arg Gly Ser Leu Gln Asp Ile Leu
        595                 600                 605

Glu Asn Asp Ser Ile Asn Leu Asp Trp Met Phe Arg Tyr Ser Leu Ile
    610                 615                 620

Asn Asp Leu Val Lys Gly Met Ala Phe Leu His Asn Ser Ile Ile Ser
625                 630                 635                 640

Ser His Gly Ser Leu Lys Ser Ser Asn Cys Val Val Asp Ser Arg Phe
            645                 650                 655

Val Leu Lys Ile Thr Asp Tyr Gly Leu Ala Ser Phe Arg Ser Thr Ala
        660                 665                 670

Glu Pro Asp Asp Ser His Ala Leu Tyr Ala Lys Lys Leu Trp Thr Ala
    675                 680                 685

Pro Glu Leu Leu Ser Gly Asn Pro Leu Pro Thr Thr Gly Met Gln Lys
690                 695                 700

Ala Asp Val Tyr Ser Phe Gly Ile Ile Leu Gln Glu Ile Ala Leu Arg
705                 710                 715                 720

Ser Gly Pro Phe Tyr Leu Glu Gly Leu Asp Leu Ser Pro Lys Glu Ile
            725                 730                 735

Val Gln Lys Val Arg Asn Gly Gln Arg Pro Tyr Phe Arg Pro Ser Ile
        740                 745                 750

Asp Arg Thr Gln Leu Asn Glu Glu Leu Val Leu Leu Met Glu Arg Cys
    755                 760                 765

Trp Ala Gln Asp Pro Ala Glu Arg Pro Asp Phe Gly Gln Ile Lys Gly
770                 775                 780

Phe Ile Arg Arg Phe Asn Lys Glu Gly Gly Thr Ser Ile Leu Asp Asn
785                 790                 795                 800

Leu Leu Leu Arg Met Glu Gln Tyr Ala Asn Asn Leu Glu Lys Leu Val
            805                 810                 815

Glu Glu Arg Thr Gln Ala Tyr Leu Glu Glu Lys Arg Lys Ala Glu Ala
        820                 825                 830

Leu Leu Tyr Gln Ile Leu Pro His Ser Val Ala Glu Gln Leu Lys Arg
    835                 840                 845

Gly Glu Thr Val Gln Ala Glu Ala Phe Asp Ser Val Thr Ile Tyr Phe
850                 855                 860

Ser Asp Ile Val Gly Phe Thr Ala Leu Ser Ala Glu Ser Thr Pro Met
865                 870                 875                 880

Gln Val Val Thr Leu Leu Asn Asp Leu Tyr Thr Cys Phe Asp Ala Ile
            885                 890                 895

Ile Asp Asn Phe Asp Val Tyr Lys Val Glu Thr Ile Gly Asp Ala Tyr
        900                 905                 910

Met Val Val Ser Gly Leu Pro Gly Arg Asn Gly Gln Arg His Ala Pro
    915                 920                 925

Glu Ile Ala Arg Met Ala Leu Ala Leu Leu Asp Ala Val Ser Ser Phe
930                 935                 940

Arg Ile Arg His Arg Pro His Asp Gln Leu Arg Leu Arg Ile Gly Val
945                 950                 955                 960

His Thr Gly Pro Val Cys Ala Gly Val Val Gly Leu Lys Met Pro Arg
            965                 970                 975

Tyr Cys Leu Phe Gly Asp Thr Val Asn Thr Ala Ser Arg Met Glu Ser
        980                 985                 990

Asn Gly Gln Ala Leu Lys Ile His  Val Ser Ser Thr Thr  Lys Asp Ala
    995                     1000                1005
```

Leu Asp Glu Leu Gly Cys Phe Gln Leu Glu Leu Arg Gly Asp Val
    1010                1015                1020

Glu Met Lys Gly Lys Gly Lys Met Arg Thr Tyr Trp Leu Leu Gly
    1025                1030                1035

Glu Arg Lys Gly Pro Pro Gly Leu Leu
    1040                1045

<210> SEQ ID NO 36
<211> LENGTH: 541
<212> TYPE: PRT
<213> ORGANISM: homo sapiens

<400> SEQUENCE: 36

Met Pro Ser Leu Leu Val Leu Thr Phe Ser Pro Cys Val Leu Gly
1               5                   10                  15

Trp Ala Leu Leu Ala Gly Gly Thr Gly Gly Gly Val Gly Gly Gly
            20                  25                  30

Gly Gly Gly Ala Gly Ile Gly Gly Arg Gln Glu Arg Glu Ala Leu
            35                  40                  45

Pro Pro Gln Lys Ile Glu Val Leu Val Leu Pro Gln Asp Asp Ser
    50                  55                  60

Tyr Leu Phe Ser Leu Thr Arg Val Arg Pro Ala Ile Glu Tyr Ala Leu
65                  70                  75                  80

Arg Ser Val Glu Gly Asn Gly Thr Gly Arg Arg Leu Leu Pro Pro Gly
                85                  90                  95

Thr Arg Phe Gln Val Ala Tyr Glu Asp Ser Asp Cys Gly Asn Arg Ala
            100                 105                 110

Leu Phe Ser Leu Val Asp Arg Val Ala Ala Arg Gly Ala Lys Pro
            115                 120                 125

Asp Leu Ile Leu Gly Pro Val Cys Glu Tyr Ala Ala Ala Pro Val Ala
            130                 135                 140

Arg Leu Ala Ser His Trp Asp Leu Pro Met Leu Ser Ala Gly Ala Leu
145                 150                 155                 160

Ala Ala Gly Phe Gln His Lys Asp Ser Glu Tyr Ser His Leu Thr Arg
                165                 170                 175

Val Ala Pro Ala Tyr Ala Lys Met Gly Glu Met Met Leu Ala Leu Phe
            180                 185                 190

Arg His His His Trp Ser Arg Ala Ala Leu Val Tyr Ser Asp Asp Lys
            195                 200                 205

Leu Glu Arg Asn Cys Tyr Phe Thr Leu Glu Gly Val His Glu Val Phe
            210                 215                 220

Gln Glu Glu Gly Leu His Thr Ser Ile Tyr Ser Phe Asp Glu Thr Lys
225                 230                 235                 240

Asp Leu Asp Leu Glu Asp Ile Val Arg Asn Ile Gln Ala Ser Glu Arg
                245                 250                 255

Val Val Ile Met Cys Ala Ser Ser Asp Thr Ile Arg Ser Ile Met Leu
            260                 265                 270

Val Ala His Arg His Gly Met Thr Ser Gly Asp Tyr Ala Phe Phe Asn
            275                 280                 285

Ile Glu Leu Phe Asn Ser Ser Ser Tyr Gly Asp Gly Ser Trp Lys Arg
            290                 295                 300

Gly Asp Lys His Asp Phe Glu Ala Lys Gln Ala Tyr Ser Ser Leu Gln
305                 310                 315                 320

Thr Val Thr Leu Leu Arg Thr Val Lys Pro Glu Phe Glu Lys Phe Ser
                325                 330                 335

```
Met Glu Val Lys Ser Ser Val Glu Lys Gln Gly Leu Asn Met Glu Asp
            340                 345                 350

Tyr Val Asn Met Phe Val Glu Gly Phe His Asp Ala Ile Leu Leu Tyr
        355                 360                 365

Val Leu Ala Leu His Glu Val Leu Arg Ala Gly Tyr Ser Lys Lys Asp
    370                 375                 380

Gly Gly Lys Ile Ile Gln Gln Thr Trp Asn Arg Thr Phe Glu Gly Ile
385                 390                 395                 400

Ala Gly Gln Val Ser Ile Asp Ala Asn Gly Asp Arg Tyr Gly Asp Phe
                405                 410                 415

Ser Val Ile Ala Met Thr Asp Val Glu Ala Gly Thr Gln Glu Val Ile
                420                 425                 430

Gly Asp Tyr Phe Gly Lys Glu Gly Arg Phe Glu Met Arg Pro Asn Val
            435                 440                 445

Lys Tyr Pro Trp Gly Pro Leu Lys Leu Arg Ile Asp Glu Asn Arg Ile
    450                 455                 460

Val Glu His Thr Asn Ser Ser Pro Cys Lys Ser Ser Gly Gly Leu Glu
465                 470                 475                 480

Glu Ser Ala Val Thr Gly Ile Val Val Gly Ala Leu Leu Gly Ala Gly
                485                 490                 495

Leu Leu Met Ala Phe Tyr Phe Phe Arg Lys Lys Tyr Arg Ile Thr Ile
                500                 505                 510

Glu Arg Arg Thr Gln Gln Glu Glu Ser Asn Leu Gly Lys His Arg Glu
            515                 520                 525

Leu Arg Glu Asp Ser Ile Arg Ser His Phe Ser Val Ala
            530                 535                 540
```